(12) United States Patent
Dadd et al.

(10) Patent No.: US 8,355,793 B2
(45) Date of Patent: Jan. 15, 2013

(54) OPTICAL NEURAL STIMULATING DEVICE HAVING A SHORT STIMULATING ASSEMBLY

(75) Inventors: Fysh Dadd, Lane Cove (AU); Jim Patrick, Roseville (AU); Bart Volckaerts, Lane Cove (AU); Edmond D. Capcelea, Bondi Junction (AU); Peter Gibson, South Coogee (AU)

(73) Assignee: Cochlear Limited, Macquarie University, NSW (AU)

( * ) Notice: Subject to any disclaimer, the term of this patent is extended or adjusted under 35 U.S.C. 154(b) by 898 days.

(21) Appl. No.: 12/348,235

(22) Filed: Jan. 2, 2009

(65) Prior Publication Data

US 2010/0174344 A1 Jul. 8, 2010

(51) Int. Cl.
*A61N 1/00* (2006.01)
*A61N 5/06* (2006.01)

(52) U.S. Cl. ............................................. 607/57; 607/88
(58) Field of Classification Search .............. 607/55–57, 607/88
See application file for complete search history.

(56) References Cited

U.S. PATENT DOCUMENTS

| | | | |
|---|---|---|---|
| 4,532,930 A | 8/1985 | Crosby et al. | |
| 5,394,865 A | 3/1995 | Salerno | |
| 6,078,838 A | 6/2000 | Rubinstein | |
| 6,295,472 B1 | 9/2001 | Rubinstein et al. | |
| 6,309,410 B1 | 10/2001 | Kuzma et al. | |
| 6,421,569 B1 | 7/2002 | Treaba et al. | |
| 6,754,537 B1 | 6/2004 | Harrison et al. | |
| 6,889,094 B1 | 5/2005 | Kuzma et al. | |
| 6,921,413 B2 | 7/2005 | Mahadevan-Jansen et al. | |
| 7,076,308 B1 | 7/2006 | Overstreet et al. | |
| 7,444,877 B2 | 11/2008 | Li et al. | |
| 8,000,798 B2 * | 8/2011 | Gantz et al. ..................... | 607/57 |
| 2002/0156513 A1 | 10/2002 | Borkan | |
| 2004/0147825 A1 | 7/2004 | Milojevic et al. | |
| 2004/0230254 A1 | 11/2004 | Harrison et al. | |
| 2006/0129210 A1 * | 6/2006 | Cantin et al. .................... | 607/88 |
| 2006/0149337 A1 | 7/2006 | John | |
| 2006/0161227 A1 | 7/2006 | Walsh, Jr. et al. | |
| 2006/0235500 A1 | 10/2006 | Gibson et al. | |
| 2007/0060984 A1 | 3/2007 | Webb et al. | |

(Continued)

FOREIGN PATENT DOCUMENTS

WO 99/41945 8/1999

(Continued)

OTHER PUBLICATIONS

International Search report issued by the International Searching Authority in connection with PCT application No. PCT/AU2003/000839, dated Aug. 5, 2003 (2 pages).

(Continued)

*Primary Examiner* — Mark W Bockelman
(74) *Attorney, Agent, or Firm* — Kilpatrick, Townsend & Stockton, LLP.

(57) ABSTRACT

A cochlear implant is provided. The cochlear implant comprises a stimulator unit configured to generate electrical stimulation signals based on sound processor-encoded signals, and to generate one or more optical stimulation signals, and an implantable stimulating assembly. The implantable stimulating assembly is configured to be implanted into a basal region of a recipient's cochlea such that when the stimulating assembly is fully implanted, a distal end of the assembly extends to the basal turn of the cochlea. The stimulating assembly also comprises: an optical contact to deliver the one or more optical stimulation signals to the cochlea, and an electrical contact to deliver the electric stimulation signals to a basal region of the cochlea so as to cause perception by the recipient of one or more frequency components of the acoustic sound signal.

47 Claims, 30 Drawing Sheets

U.S. PATENT DOCUMENTS

| | | |
|---|---|---|
| 2007/0203557 A1 | 8/2007 | Gantz et al. |
| 2007/0244522 A1 | 10/2007 | Overstreet |
| 2009/0054954 A1 | 2/2009 | Foley et al. |
| 2010/0174330 A1 | 7/2010 | Dadd et al. |

FOREIGN PATENT DOCUMENTS

| | | |
|---|---|---|
| WO | 02/071984 | 9/2002 |
| WO | 03/035168 | 5/2003 |
| WO | WO-2007/013891 | 10/2007 |

OTHER PUBLICATIONS

International Preliminary Examination Report issued by the International Preliminary Examining Authority in connection with PCT application No. PCT/AU2003/000839, dated Oct. 26, 2004 (6 pages).

Lithgow, "Potential Advantages of High Pulse Rate Stimulation of Cochlear Implants," $2^{nd}$ International Conference on Bioelectromagnetism, Melbourne, Australia, Feb. 1998.

* cited by examiner

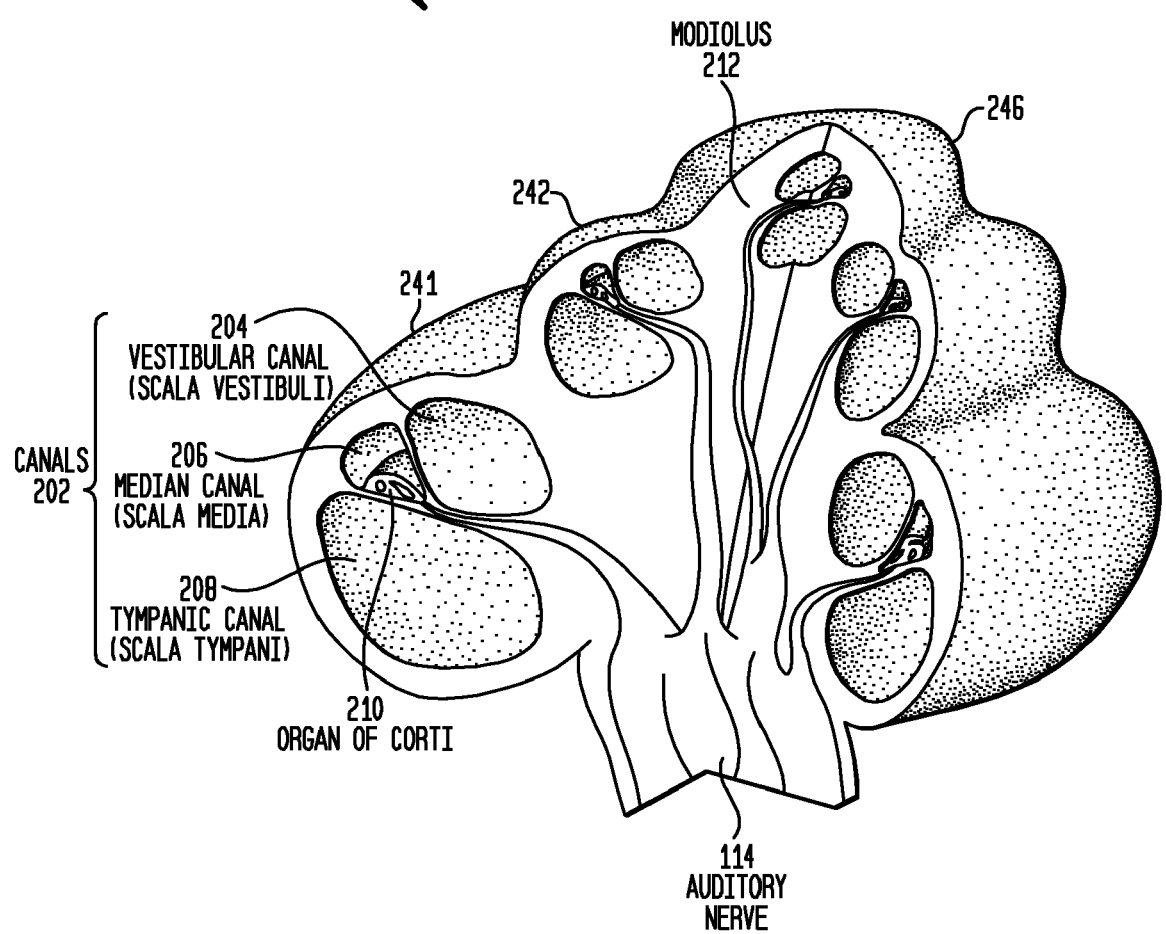

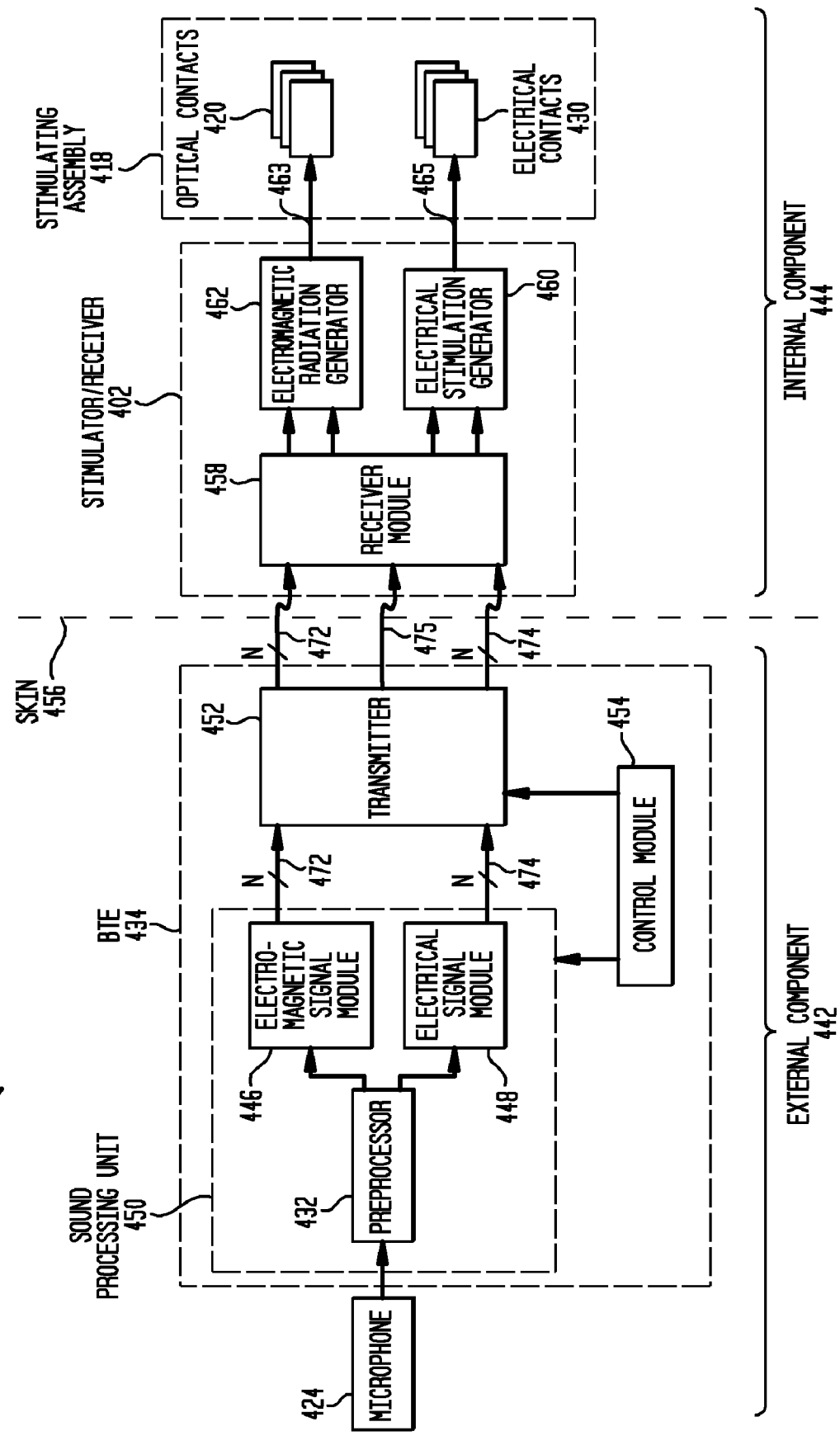

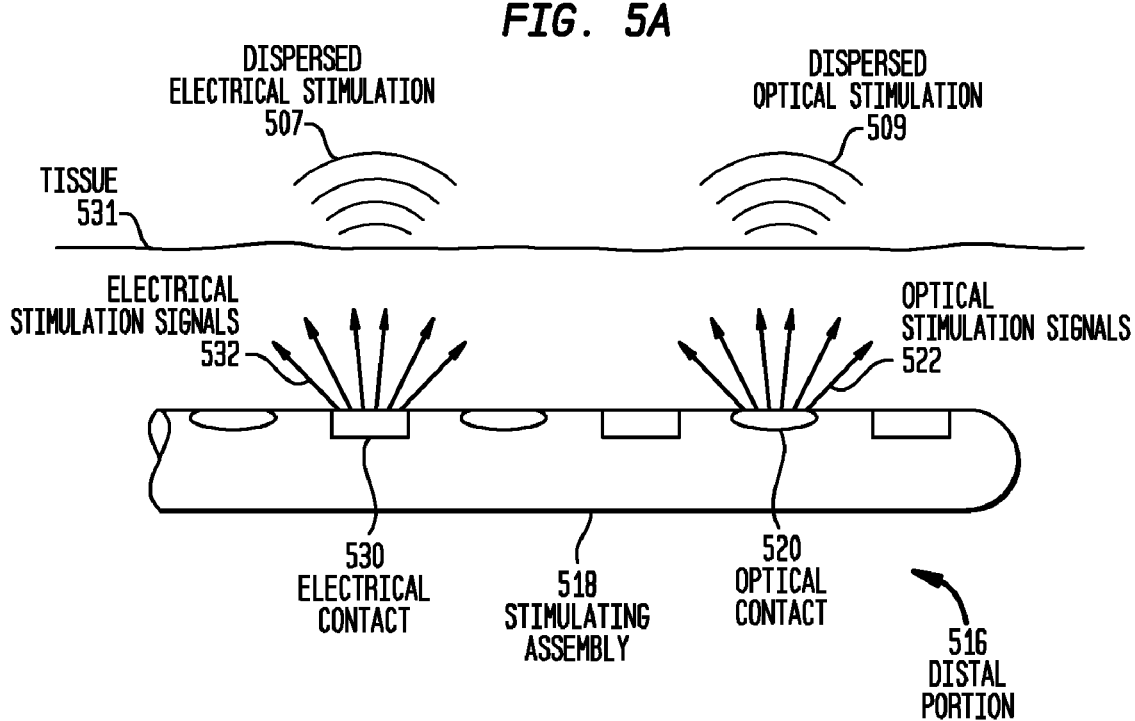
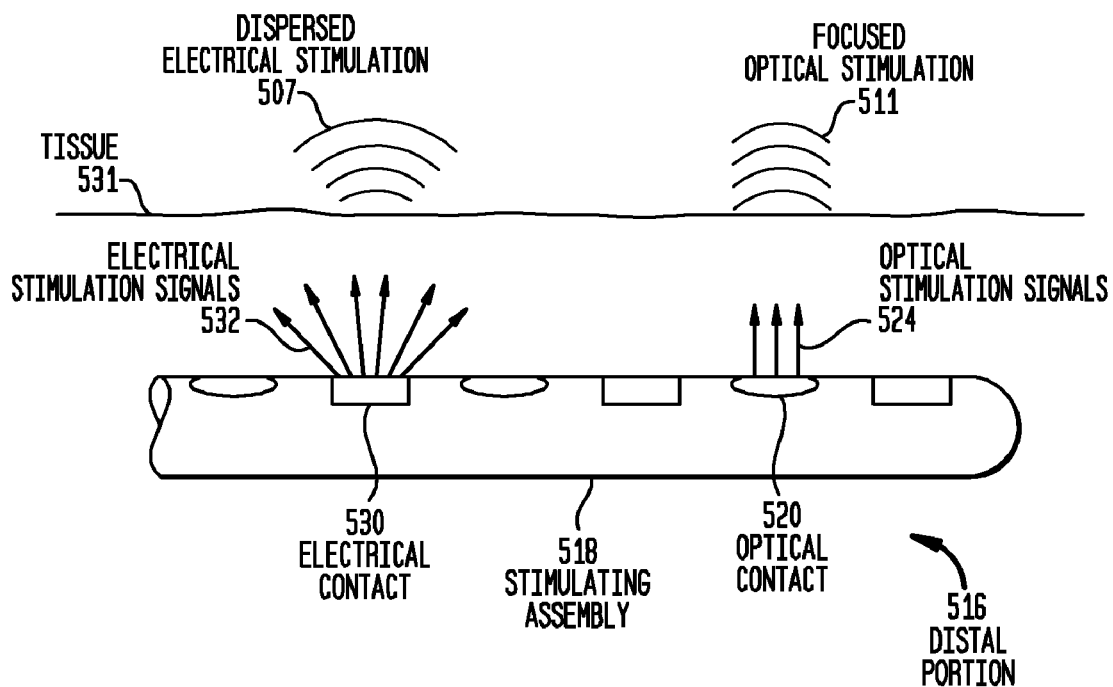

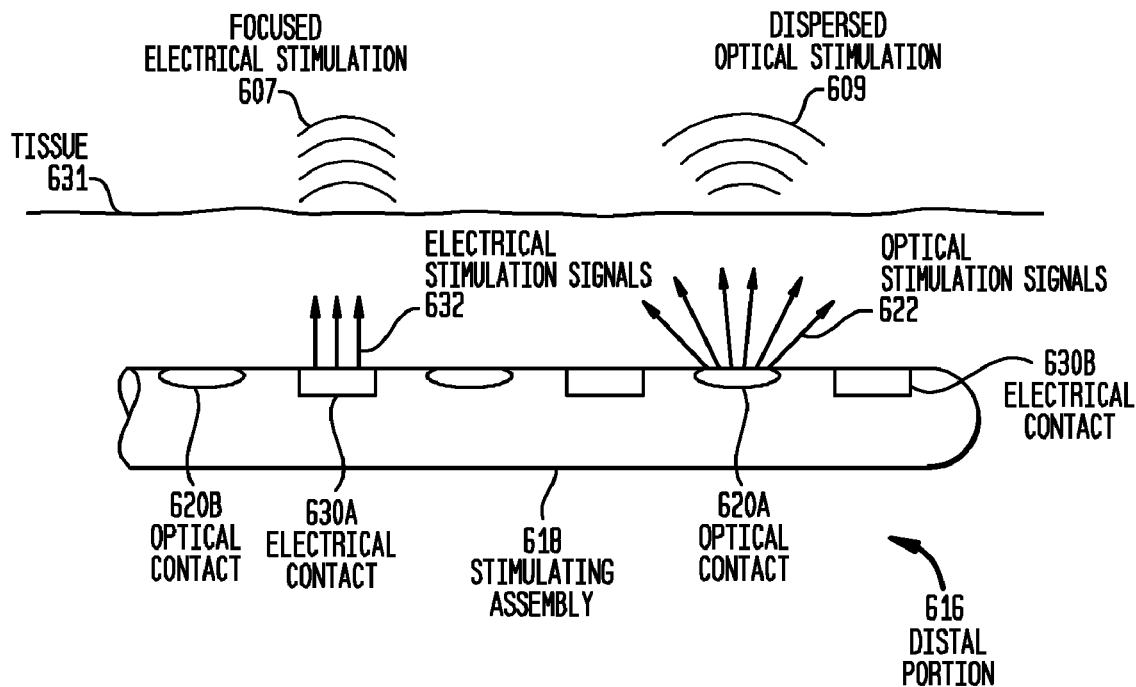
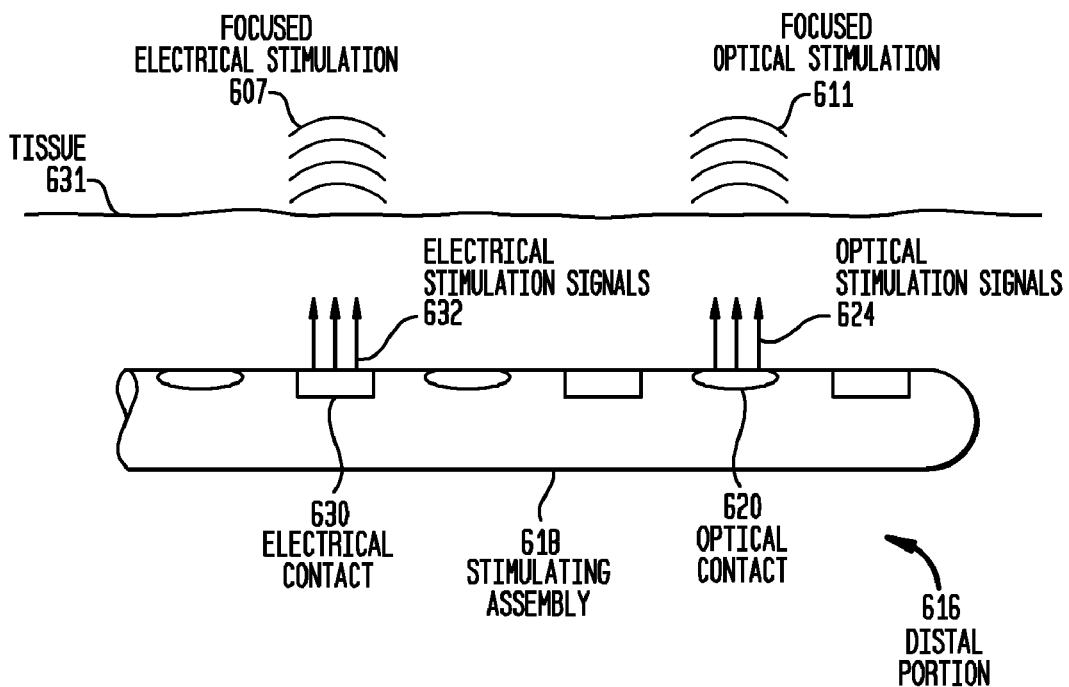

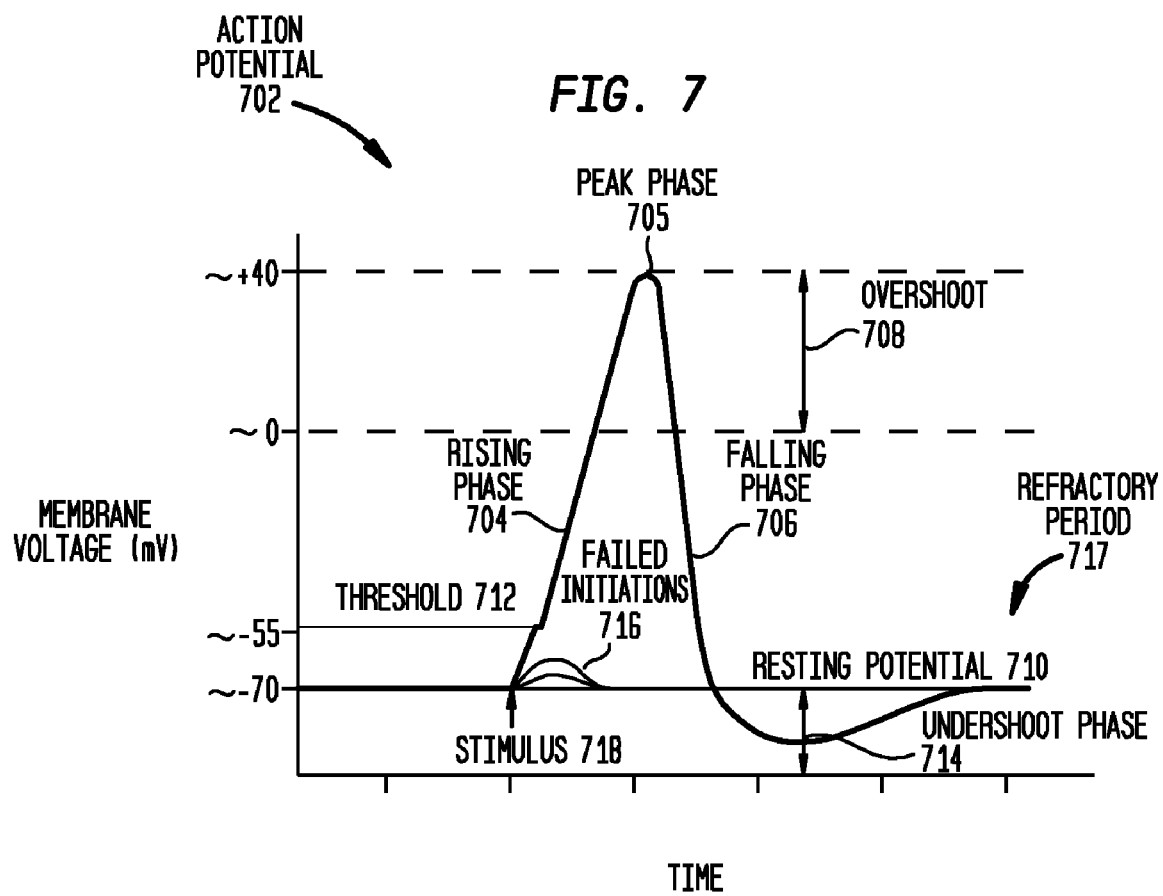

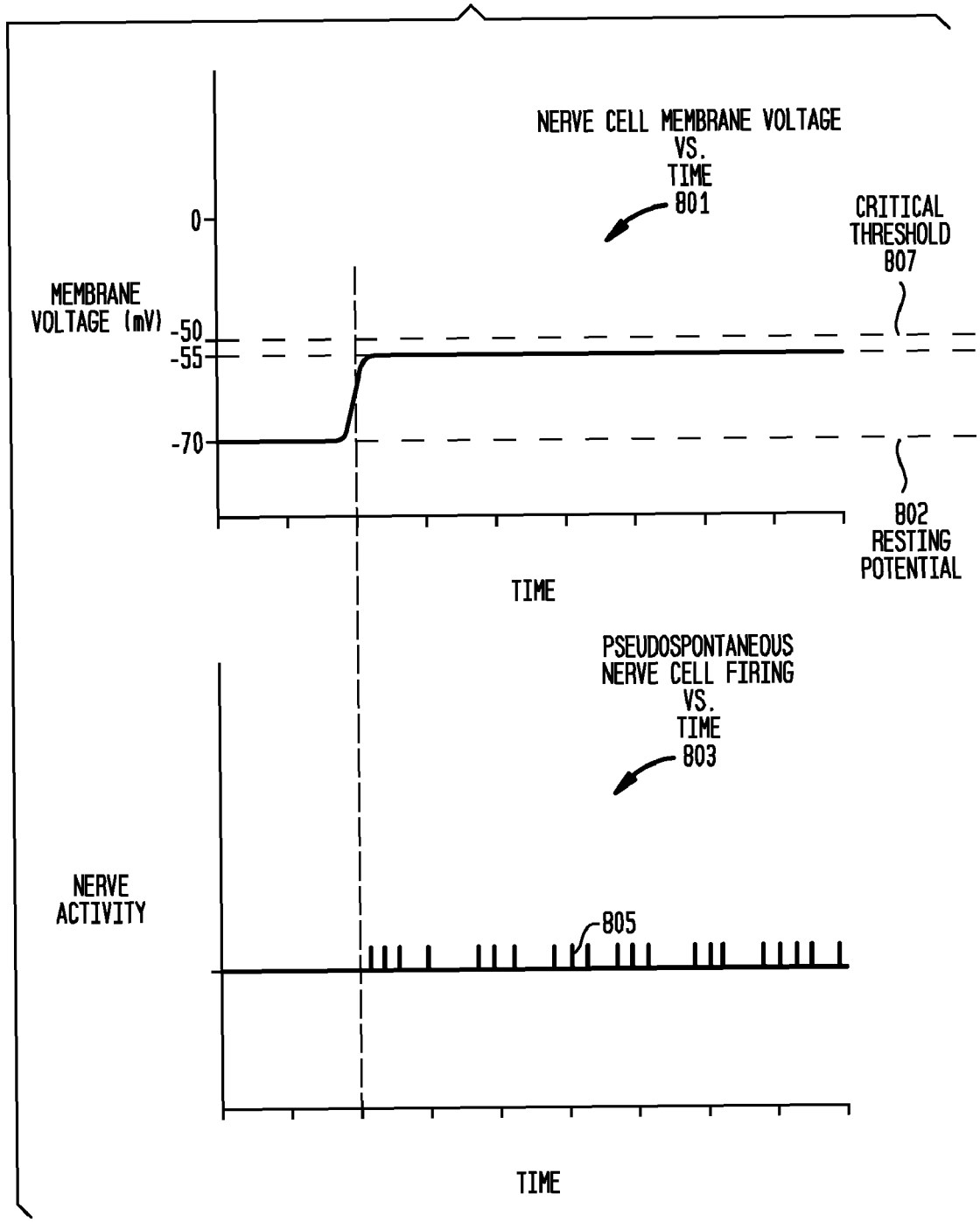

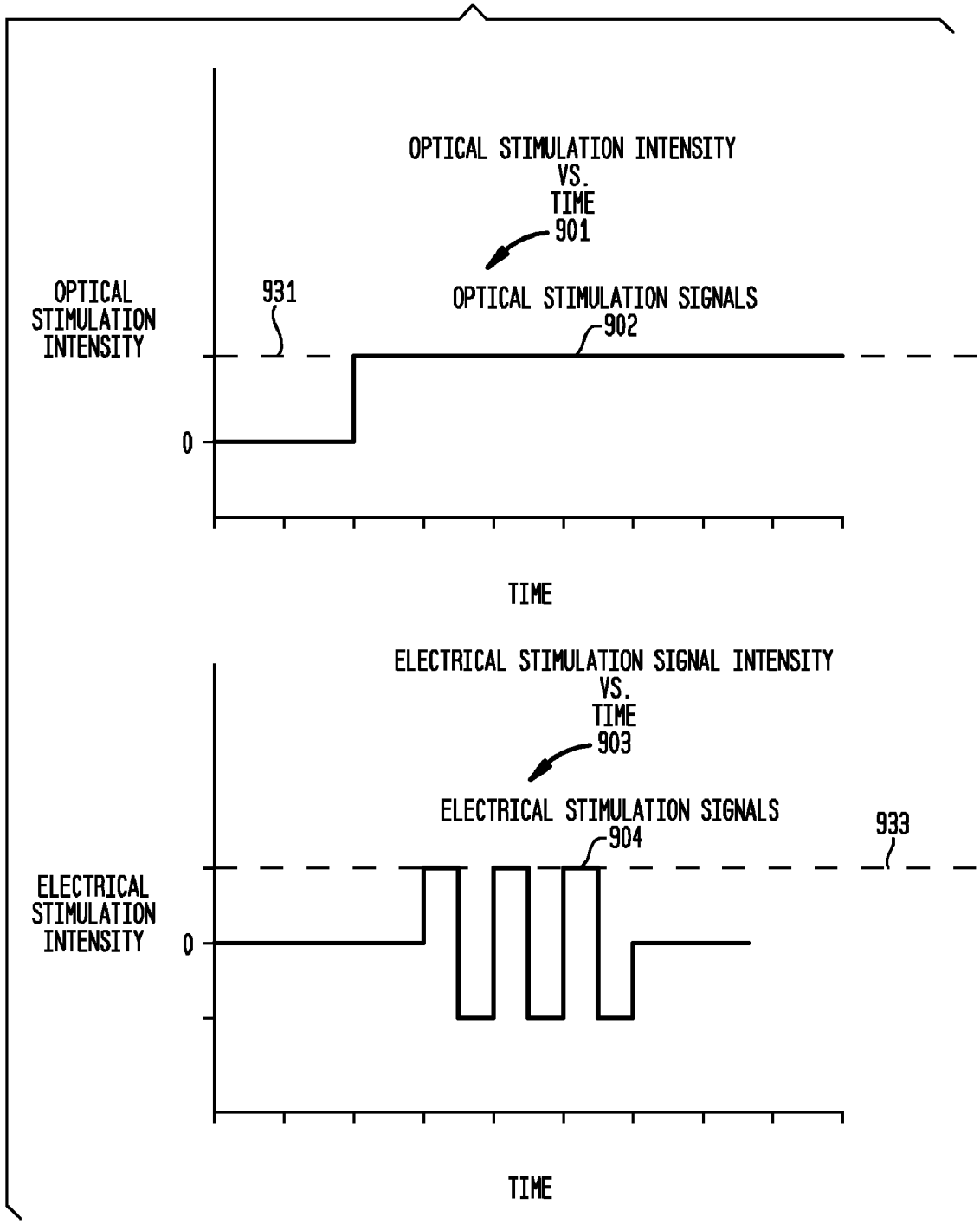

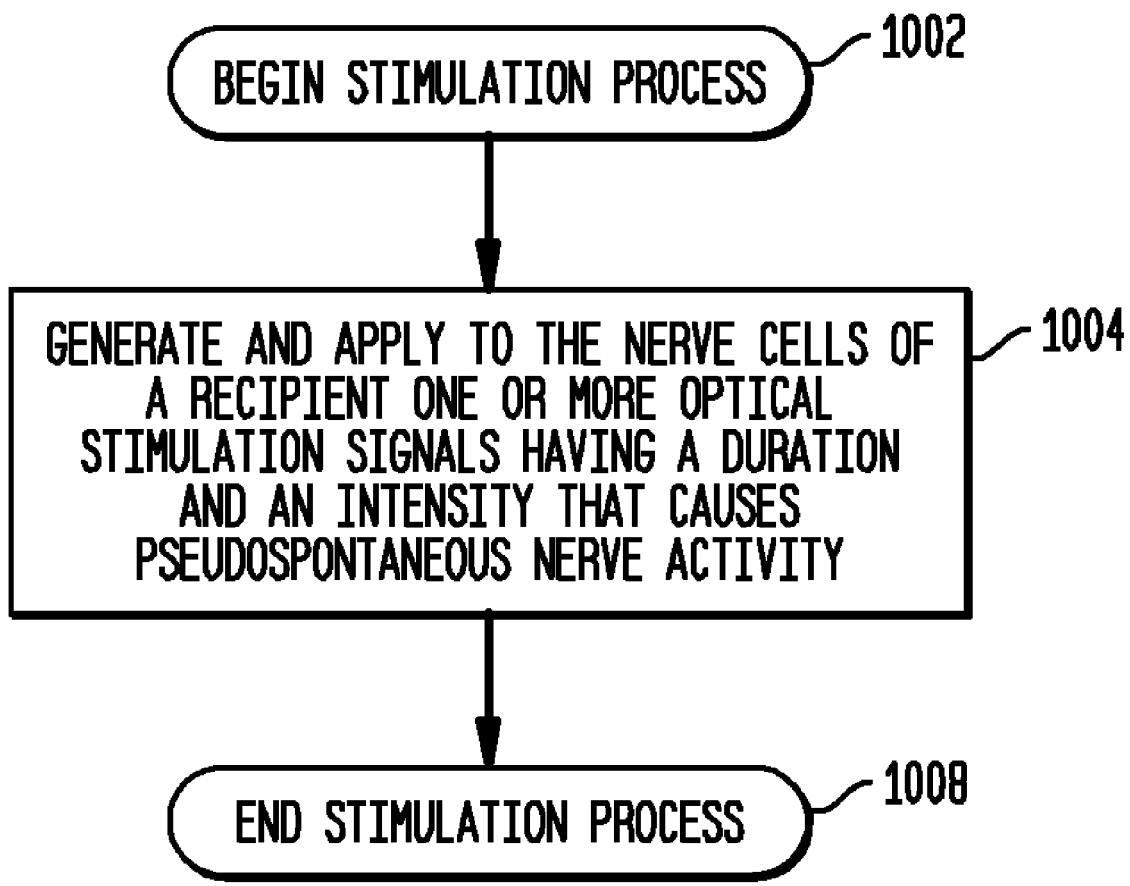

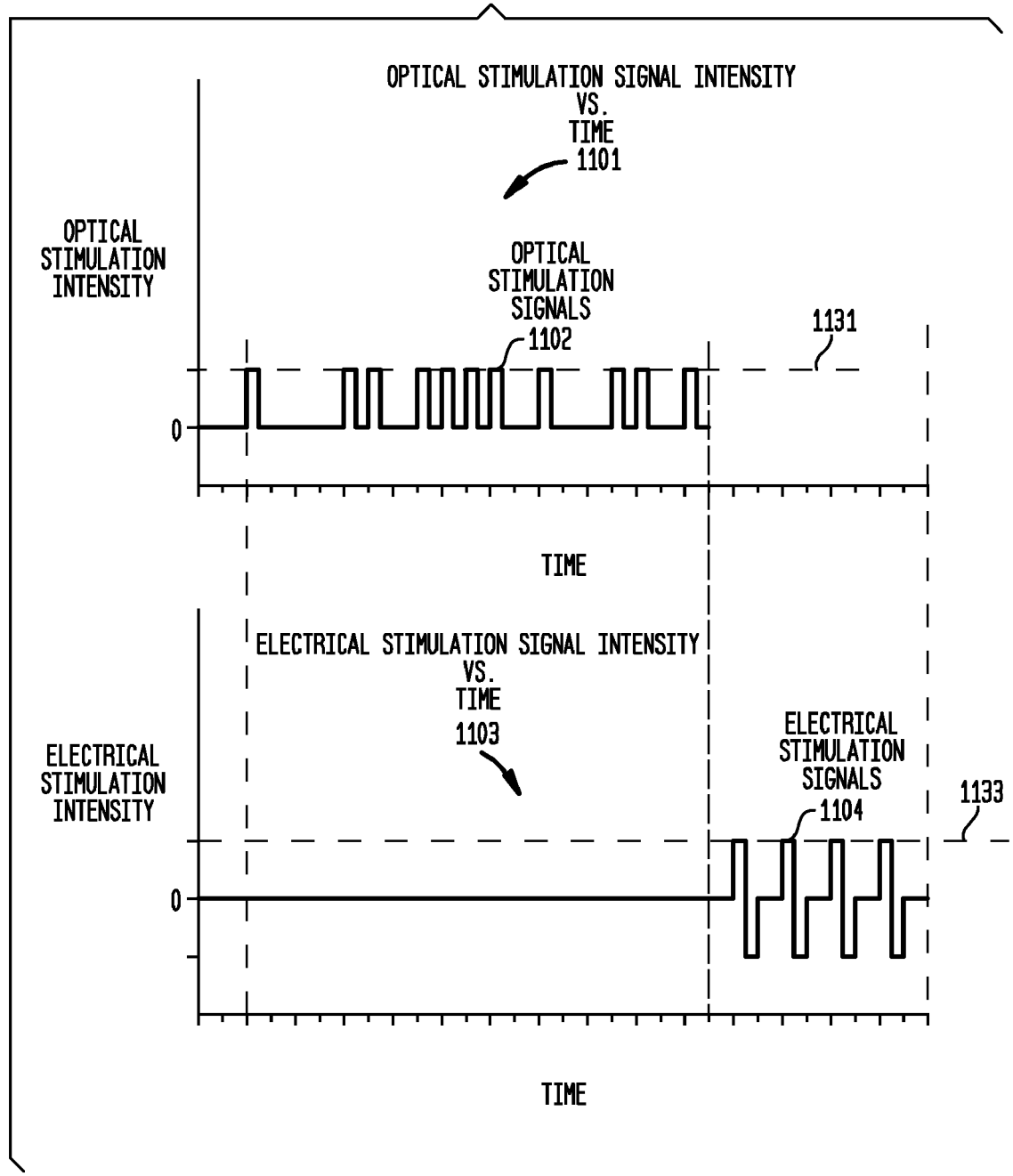

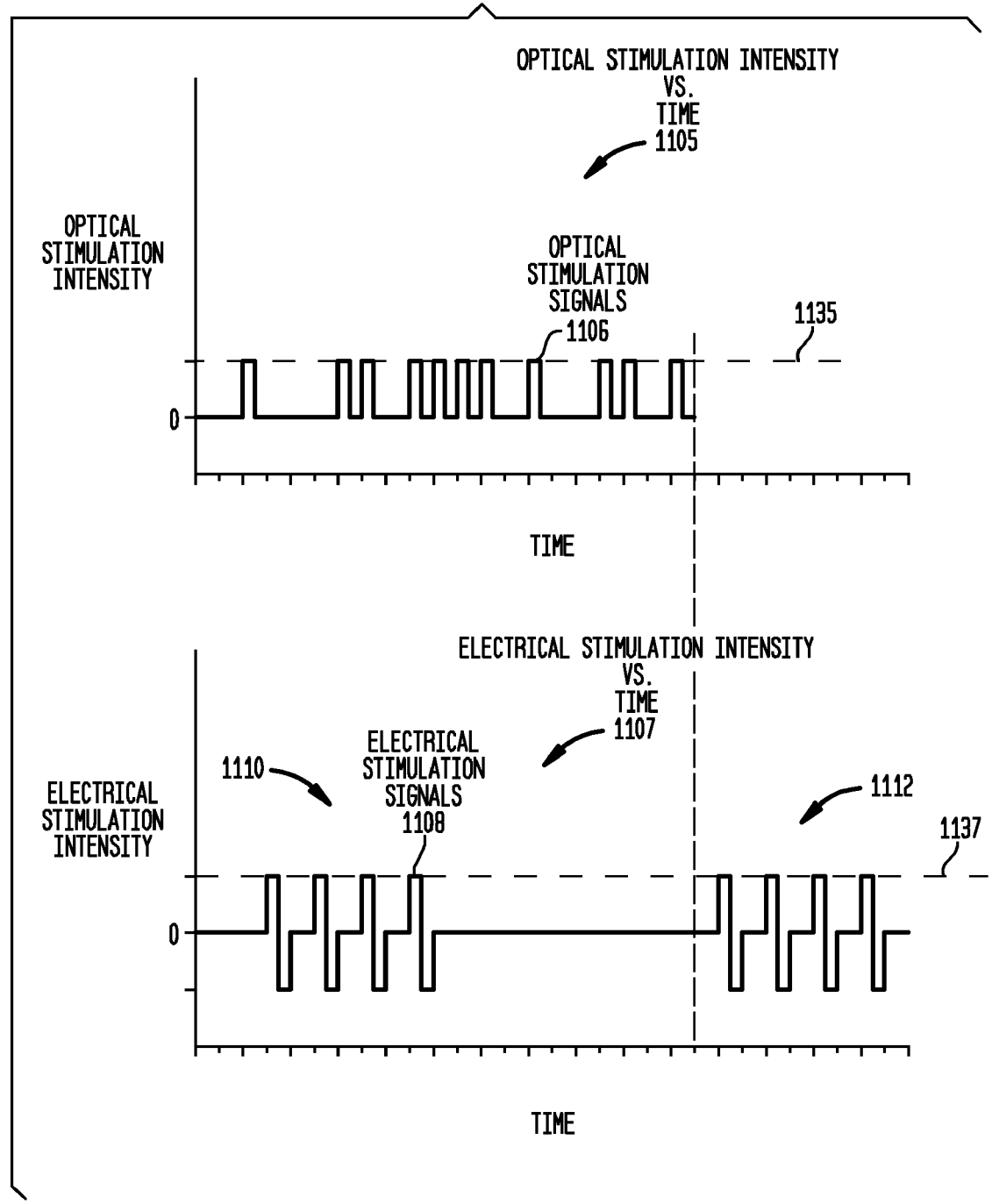

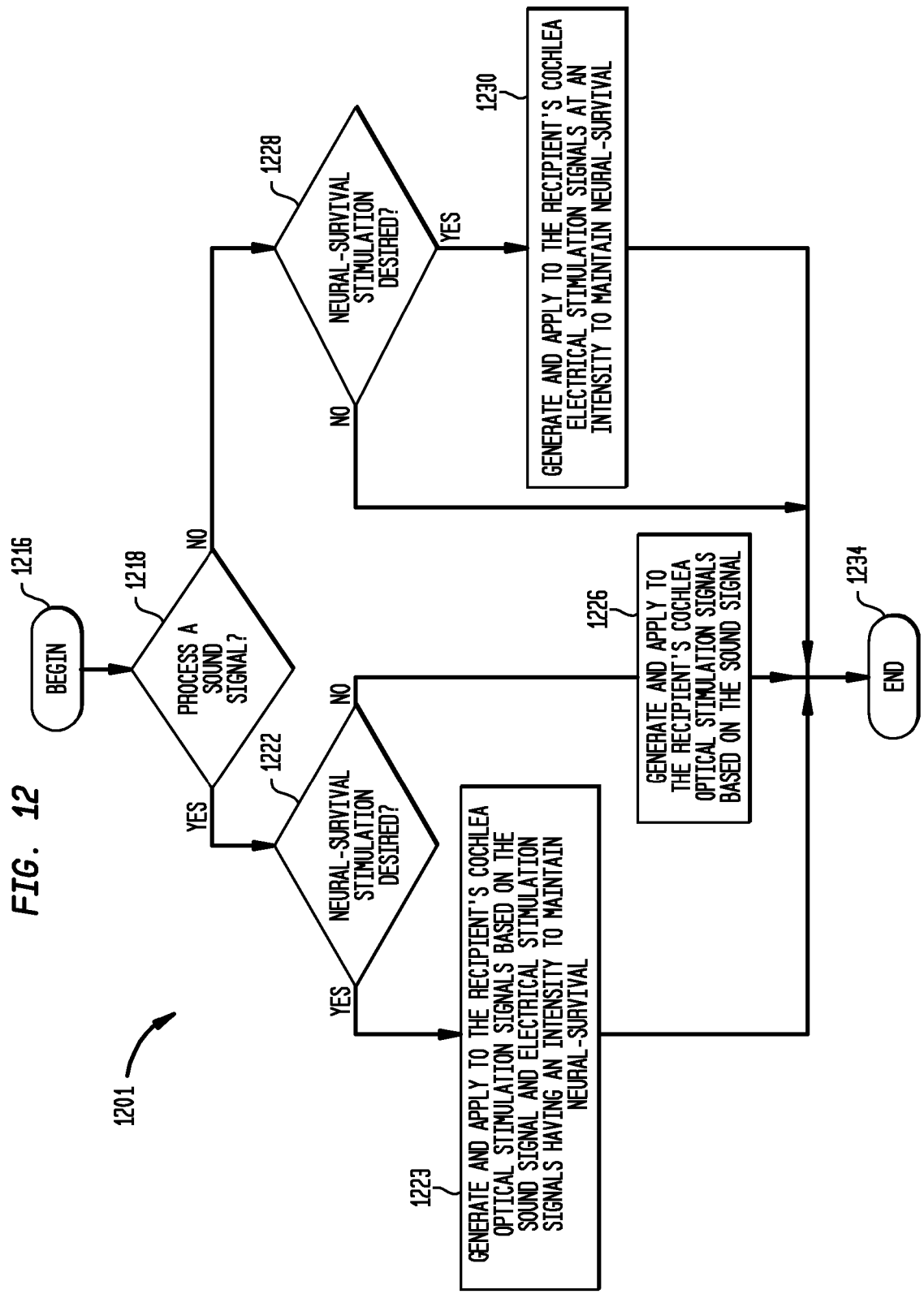

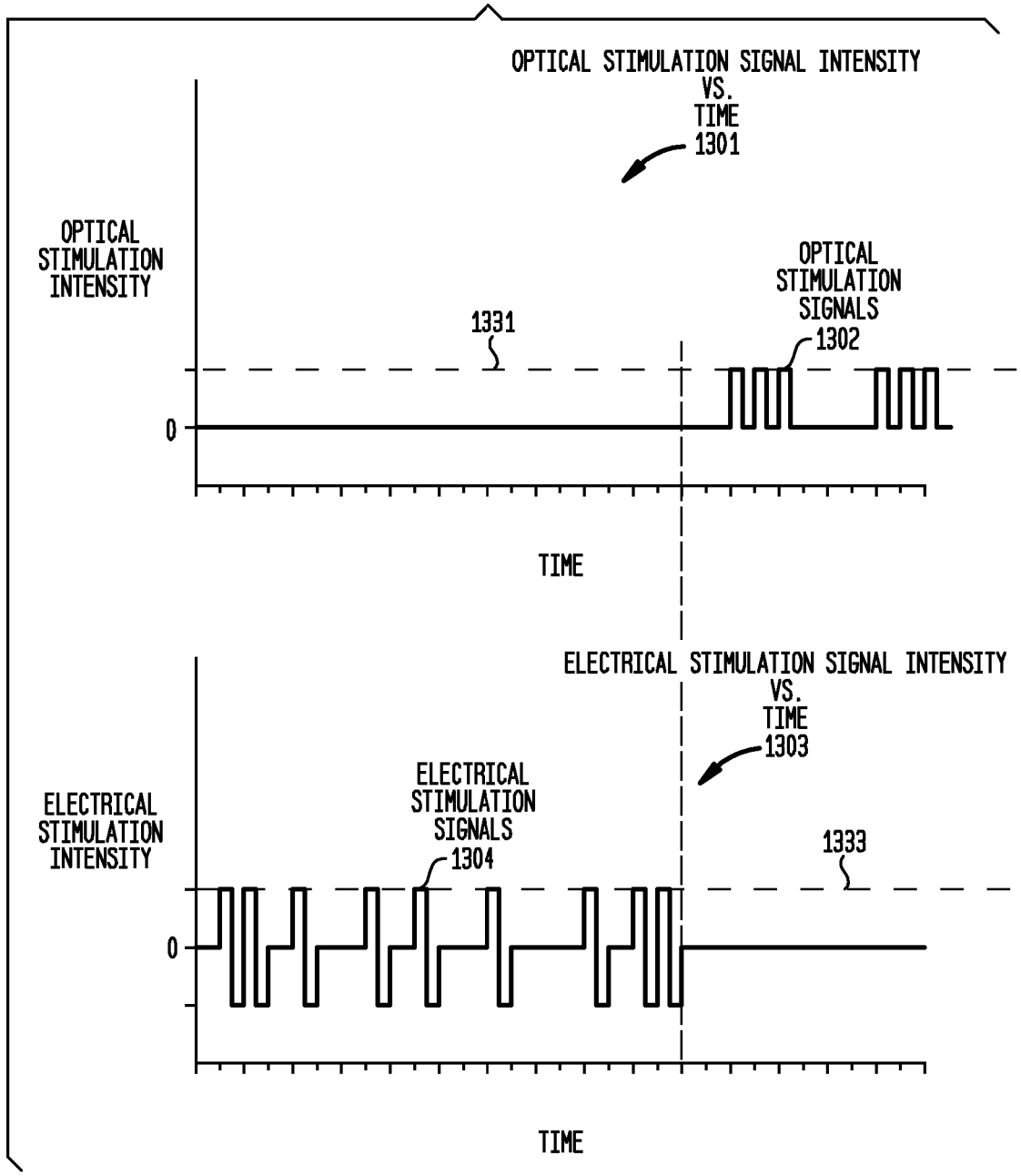

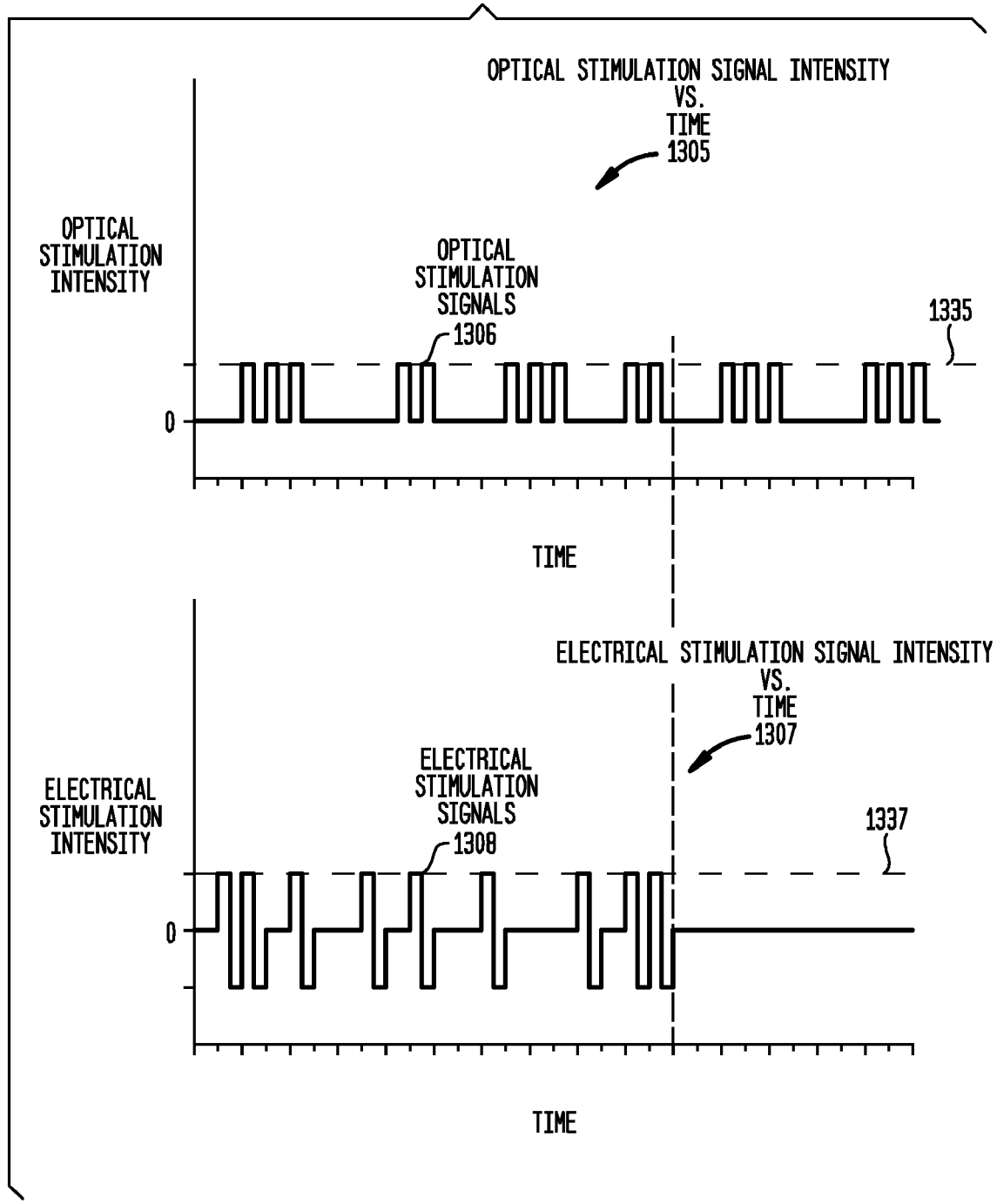

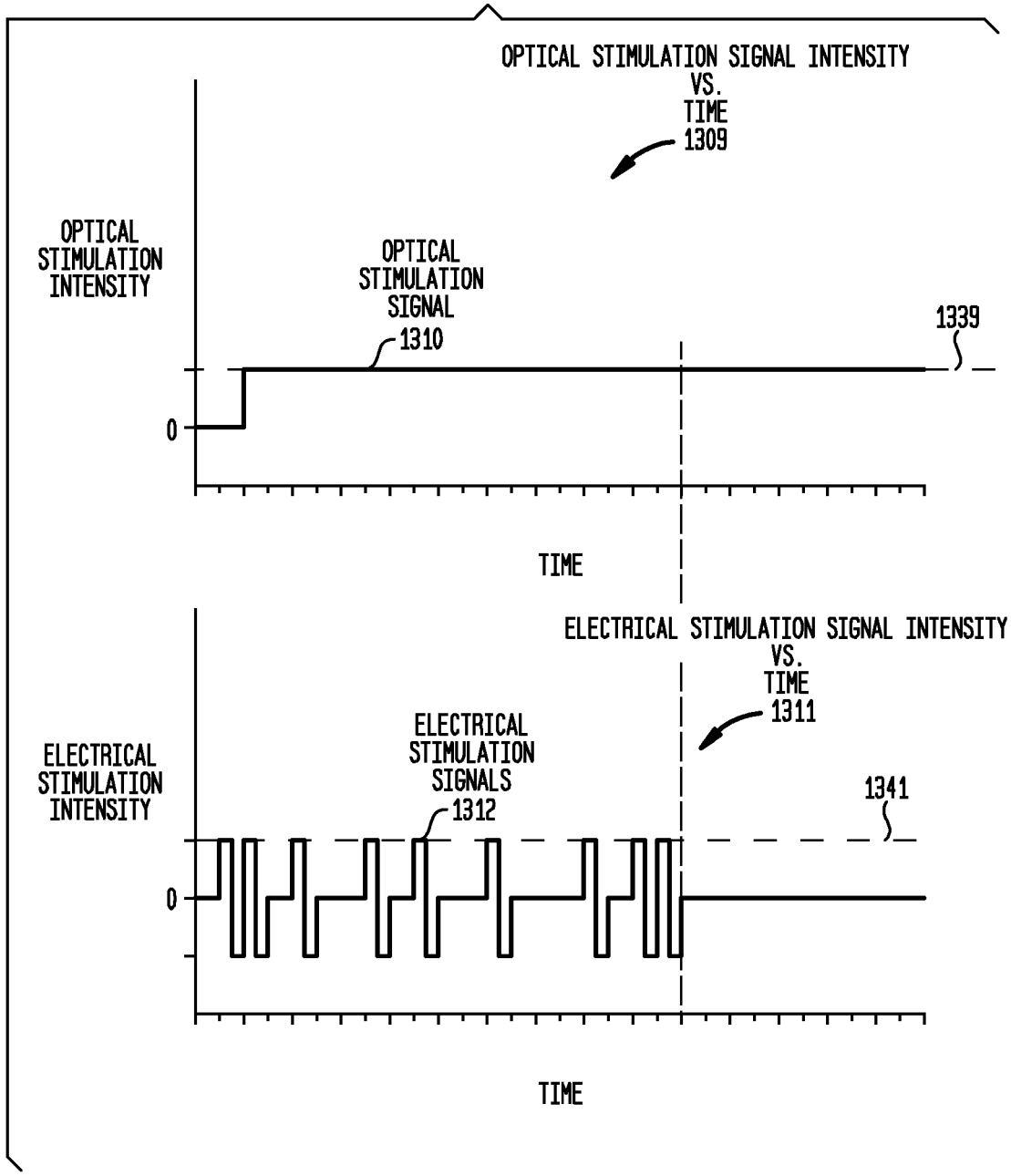

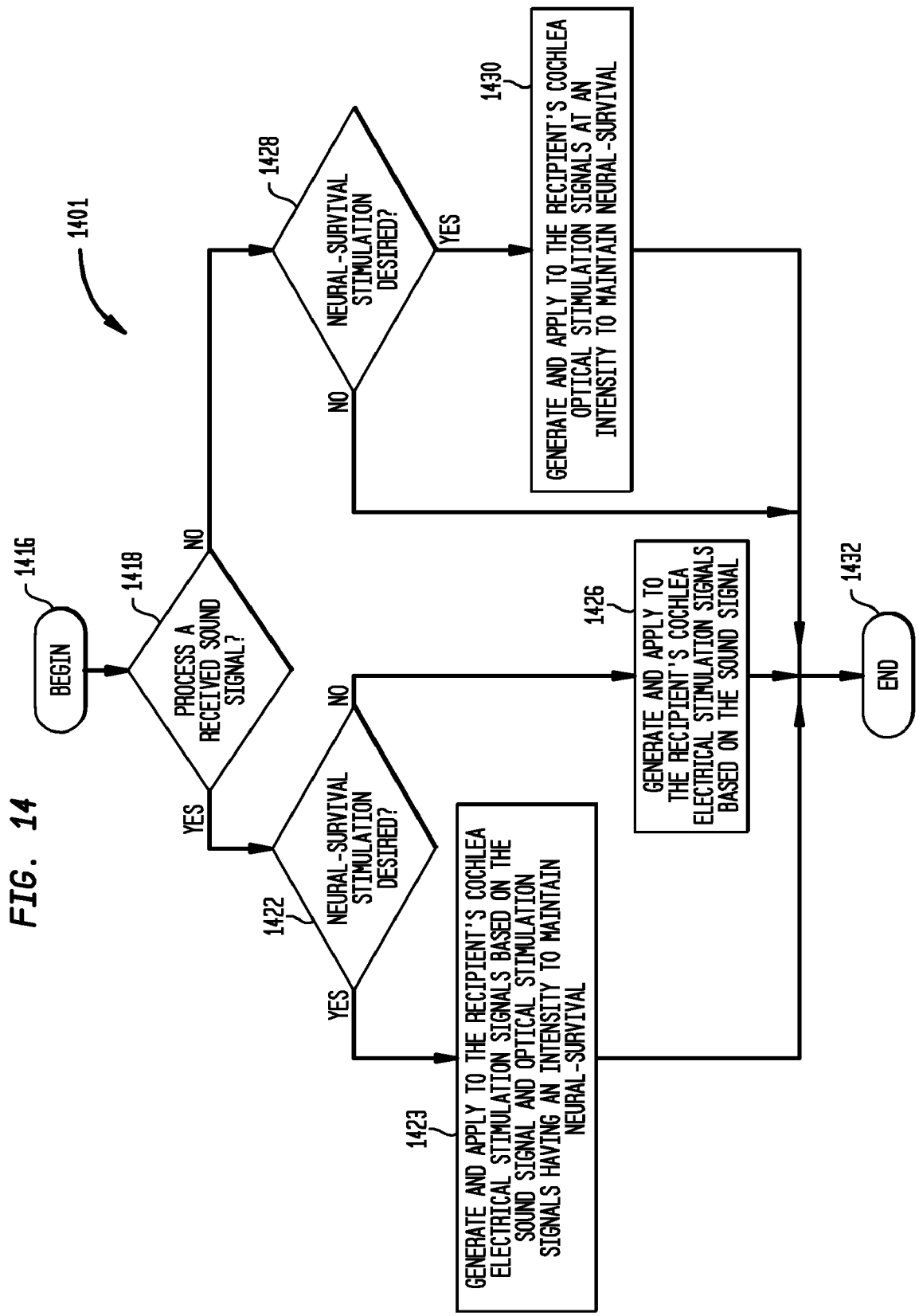

2710
POSITIVE (CONVERGING) LENS

2712
NEGATIVE (DIVERGING) LENS

OPTICAL NEURAL STIMULATING DEVICE HAVING A SHORT STIMULATING ASSEMBLY

CROSS-REFERENCE TO RELATED APPLICATIONS

This application is a related to commonly owned and co-pending U.S. patent application entitled "A NEURAL-STIMULATING DEVICE FOR GENERATING PSEUDO-SPONTANEOUS NEURAL ACTIVITY," and commonly owned and co-pending U.S. patent application entitled "COMBINED OPTICAL AND ELECTRICAL NEURAL STIMULATION," both filed concurrently herewith. Both of these applications are hereby incorporated by reference herein in their entirety.

BACKGROUND

1. Field of the Invention

The present invention relates generally to stimulating medical devices and, more particularly, to an optical neural stimulating device having a short stimulating assembly.

2. Related Art

Hearing loss, which may be due to many different causes, is generally of two types, conductive and sensorineural. In some cases, a person may have hearing loss of both types. Conductive hearing loss occurs when the normal mechanical pathways for sound to reach the hair cells in the cochlea are impeded, for example, by damage to the ossicles. Conductive hearing loss is often addressed with conventional hearing aids which amplify sound so that acoustic information can reach the cochlea.

In many people who are profoundly deaf, however, the reason for their deafness is sensorineural hearing loss. Sensorineural hearing loss occurs when there is damage to the inner ear or to the nerve pathways from the inner ear to the brain. Those suffering from sensorineural hearing loss are thus unable to derive suitable benefit from conventional hearing aids. As a result, specific neural-stimulating devices, referred to herein as electrically-stimulating auditory prostheses, have been developed to provide persons having sensorineural hearing loss with the ability to perceive sound. Such electrically-stimulating auditory prostheses deliver electrical stimulation to nerve cells of the recipient's auditory system.

As used herein, the recipient's auditory system includes all sensory system components used to perceive a sound signal, such as hearing sensation receptors, neural pathways, including the auditory nerve and spiral ganglion, and parts of the brain used to sense sounds. Electrically-stimulating auditory prostheses include, for example, auditory brain stimulators and Cochlear™ prostheses (commonly referred to as Cochlear™ prosthetic devices, Cochlear™ implants, Cochlear™ devices, and the like; simply "cochlear implants" herein.)

Most sensorineural hearing loss is due to the absence or destruction of the cochlear hair cells which transduce acoustic signals into nerve impulses. It is for this purpose that cochlear implants have been developed. Cochlear implants use direct electrical stimulation of auditory nerve cells to bypass absent or defective hair cells that normally transduce acoustic vibrations into neural activity. Such devices generally use an electrode array implanted into the scala tympani of the cochlea so that the electrodes may differentially activate auditory neurons that normally encode differential pitches of sound.

Auditory brain stimulators are used to treat a smaller number of recipients with, for example, bilateral degeneration of the auditory nerve. For such recipients, the auditory brain stimulator provides stimulation of the cochlear nucleus in the brainstem.

SUMMARY

In one aspect of the present invention a cochlear implant is provided. The cochlear implant comprises: a stimulator unit configured to generate electrical stimulation signals based on sound processor-encoded signals, and to generate one or more optical stimulation signals; and an implantable stimulating assembly configured to be implanted into a basal region of a recipient's cochlea such that when the stimulating assembly is fully implanted a distal end of the assembly extends to the first turn of the cochlea, the stimulating assembly comprising: an optical contact positioned on the stimulating assembly configured to deliver the one or more optical stimulation signals to the cochlea, and an electrical contact positioned on the stimulating assembly configured to deliver the electric stimulation signals to a basal region of the cochlea so as to cause perception by the recipient of one or more frequency components of the acoustic sound signal.

In another aspect of the present invention, a method for stimulating a recipient's cochlea using a cochlear implant having a stimulating assembly configured such that when the assembly is fully implanted a distal end of the assembly extends to the first turn of the cochlea is provided. The method comprises: generating electrical stimulation signals based on a set of encoded signals; delivering the electric stimulation signals to a basal region of the cochlea so as to cause perception by the recipient of one or more frequency components of the acoustic sound signal; generating one or more optical stimulation signals; and delivering the one or more optical stimulation signals to the cochlea.

BRIEF DESCRIPTION OF THE DRAWINGS

Embodiments of the present invention are described below with reference to the attached drawings, in which:

FIG. 2A is a perspective, partially cut-away view of a cochlea exposing the canals and nerve fibers of the cochlea;

FIG. 4 is a detailed functional block diagram illustrating the components of a cochlear implant in accordance with embodiments of the present invention;

FIG. 5A is a side view of a distal region of a stimulating assembly schematically illustrating the spread of optical and electrical stimulation in accordance with embodiments of the present invention;

FIG. 5B is a side view of a distal region of a stimulating assembly schematically illustrating the spread of optical and electrical stimulation in accordance with embodiments of the present invention;

FIG. 6A is a side view of a distal region of a stimulating assembly schematically illustrating the spread of optical and electrical stimulation in accordance with embodiments of the present invention;

FIG. 6B is a side view of a distal region of a stimulating assembly schematically illustrating the spread of optical and electrical stimulation in accordance with embodiments of the present invention;

FIG. 7 is graph illustrating the various phases of an idealized action potential as the potential passes through a nerve cell, illustrated in membrane voltage versus time;

FIG. 8 diagram illustrating the membrane voltage versus time of a recipient's nerve cells along with the resulting nerve activity;

FIG. 9 is a diagram illustrating exemplary optical and electrical stimulation signals used to stimulate a recipient's nerve cells in accordance with embodiments of the present invention;

FIG. 10A is a high level flowchart illustrating operations that may be performed to encourage, facilitate or allow pseudospontaneous nerve activity to occur using optical stimulation in accordance with embodiments of the present invention;

FIG. 11A is a diagram illustrating exemplary optical and electrical stimulation signals used to stimulate a recipient's nerve cells in accordance with embodiments of the present invention;

FIG. 11B is a diagram illustrating exemplary optical and electrical stimulation signals used to stimulate a recipient's nerve cells in accordance with embodiments of the present invention;

FIG. 12 is a flowchart illustrating the operations performed in a cochlear implant in accordance with embodiments of the present invention;

FIG. 13A is a diagram illustrating exemplary optical and electrical stimulation signals used to stimulate a recipient's nerve cells in accordance with embodiments of the present invention;

FIG. 13B is a diagram illustrating exemplary optical and electrical stimulation signals used to stimulate a recipient's nerve cells in accordance with embodiments of the present invention;

FIG. 13C is a diagram illustrating exemplary optical and electrical stimulation signals used to stimulate a recipient's nerve cells in accordance with embodiments of the present invention;

FIG. 14 is a flowchart illustrating the operations performed in a cochlear implant in accordance with embodiments of the present invention;

DETAILED DESCRIPTION

Figure 1:
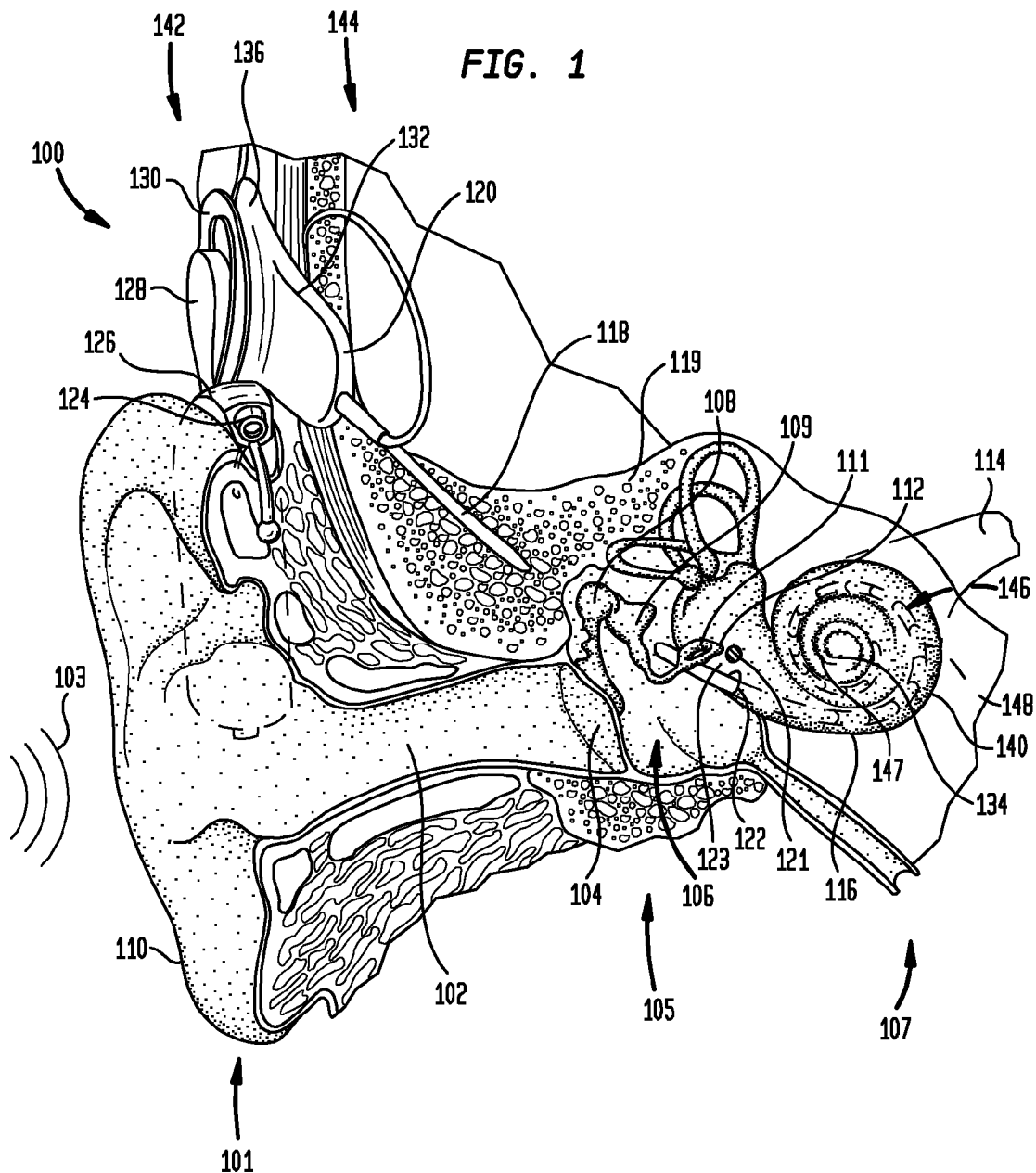
FIG. 1 is a perspective view of an implanted cochlear implant which may be advantageously configured to implement embodiments of the present invention.

Aspects of the present invention are directed to a cochlear implant having a stimulating assembly configured to be fully implanted only into a basal region of a recipient's cochlea. A cochlear implant having such a short stimulating assembly is advantageously used to treat the portion of the hearing impaired population who have the ability to perceive low frequency sounds, but who suffer from high frequency sensorineual hearing loss. Such a cochlear implant may also be advantageously used in individuals who have progressive hearing in the mid to low frequency ranges.

A cochlear implant in accordance with embodiments of the present invention comprises an electromagnetic radiation (EMR) generator to generate optical stimulation signals. The short stimulating assembly comprises optical contacts configured to apply the optical stimulation signals to the cochlea of the recipient. In specific embodiments, the cochlear implant further comprises an electrical stimulation generator to generate electrical stimulation signals, and the short stimulating assembly comprises electrical contacts to deliver the electrical stimulation signals to the cochlea of the recipient.

As used herein, optical stimulation signals consist of pulses of electromagnetic radiation. The electromagnetic radiation is not limited to the portion of the electromagnetic spectrum that is visible to the human eye, commonly referred to as the optical or visible spectrum. Rather, the electromagnetic radiation may comprise other portions of the electromagnetic spectrum such as the ultraviolet, visible, infrared, far infrared or deep infrared radiation.

Embodiments of the present invention are described herein primarily in connection with one type of neural-stimulating device, namely electrically-stimulating auditory prostheses. Electrically-stimulating auditory prostheses deliver electrical stimulation to one or more nerve cells of the recipient's auditory system. As used herein, the recipient's auditory system includes all sensory system components used to perceive a sound signal, such as hearing sensation receptors, neural pathways, including the auditory nerve and spiral ganglion, and parts of the brain used to sense sounds. As such, electrically-stimulating auditory prostheses include, for example, auditory brain stimulators and cochlear implants.

As noted, cochlear implants stimulate auditory nerve cells, bypassing absent or defective hair cells that normally transduce acoustic vibrations into neural activity. Cochlear implants generally use an array of electrodes inserted into or adjacent the cochlea so that the electrodes may activate auditory neurons that normally encode differential pitches of sound. Auditory brain stimulators are used to treat a smaller number of recipients, such as those with bilateral degeneration of the auditory nerve. The auditory brain stimulator comprises an array of electrodes configured to be positioned, for example, proximal to the recipient's brainstem. When implanted, the electrodes apply electrical stimulation signals to the cochlear nucleus in the brainstem, resulting in a hearing sensation by the recipient. Although embodiments of the present invention are described herein with reference to such electrically-stimulating auditory prostheses, it should be appreciated that embodiments of the present invention, regardless of whether described herein, may be implemented in any neural-stimulating device now known or later developed.

FIG. 1 is perspective view of an electrically-stimulating auditory prosthesis, namely a cochlear implant. An exemplary cochlear implant 100 is shown implanted in a recipient, in which embodiments of the present invention may be implemented. The relevant components of outer ear 101, middle ear 105 and inner ear 107 are described next below, followed by a description of cochlear implant 100.

In a fully functional ear, outer ear 101 comprises an auricle 110 and an ear canal 102. An acoustic pressure or sound wave 103 is collected by auricle 110 and channeled into and through ear canal 102. Disposed across the distal end of ear canal 102 is a tympanic membrane 104 which vibrates in response to sound wave 103. This vibration is coupled to oval window or fenestra ovalis 112 through three bones of middle ear 105, collectively referred to as the ossicles 106 and comprising the malleus 108, the incus 109 and the stapes 111. Bones 108, 109 and 111 of middle ear 105 serve to filter and amplify sound wave 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside cochlea 140. Activation of the hair cells causes appropriate nerve impulses to be generated and transferred through the spiral ganglion cells (not shown) and auditory nerve 114 to the brain (also not shown) where they are perceived as sound.

Cochlear implant 100 comprises an external component 142 which is directly or indirectly attached to the body of the recipient, and an internal component 144 which is temporarily or permanently implanted in the recipient. External component 142 typically comprises one or more acoustic pickup devices, such as microphone 124, for detecting sound, a sound processing unit 126, a power source (not shown), and an external transmitter unit 128. External transmitter unit 128 comprises an external coil 130 and, preferably, a magnet (not shown) secured directly or indirectly to external coil 130. Sound processing unit 126 processes the output of microphone 124 that is positioned, in the depicted embodiment, adjacent auricle 110 of the recipient. Sound processing unit 126 generates encoded signals, sometimes referred to herein as encoded data signals, which are provided to external transmitter unit 128 via a cable (not shown).

Internal component 144 comprises, in this depicted embodiment, an internal receiver unit 132, a stimulator unit 120, and an elongate stimulating assembly 118. Internal receiver unit 132 comprises an internal coil 136, and preferably, a magnet (also not shown) fixed relative to the internal coil. Internal receiver unit 132 and stimulator unit 120 are hermetically sealed within a biocompatible housing, sometimes collectively referred to as a stimulator/receiver unit. The magnets facilitate the operational alignment of the external and internal coils, enabling internal coil 136 to receive power and stimulation data from external coil 130, as noted above. Elongate stimulating assembly 118 has a proximal end connected to stimulator unit 120, and a distal end implanted in cochlea 140. Stimulating assembly 118 extends from stimulator unit 120 to cochlea 140 through mastoid bone 119. Stimulating assembly 118 is implanted into cochlea 104. As described below, stimulating assembly is implanted in cochlea 140. In some embodiments, stimulating assembly 118 may be implanted at least in basal region 116, and sometimes further. For example, stimulating assembly 118 may extend towards apical end of cochlea 140, referred to as cochlea apex 134. In certain circumstances, stimulating assembly 118 may be inserted into cochlea 140 via a cochleostomy 122. In other circumstances, a cochleostomy may be formed through round window 121, oval window 112, the promontory 123 or through an apical turn 147 of cochlea 140.

Stimulating assembly 118 comprises a longitudinally aligned and distally extending array 146 of stimulating contacts 148, sometimes referred to as contact array 146 herein, disposed along a length thereof Although contact array 146 may be disposed on stimulating assembly 118, in most practical applications, contact array 146 is integrated into stimulating assembly 118. As such, for all embodiments of stimulating assembly 118, contact array 146 is generally referred to herein as being disposed in stimulating assembly 118. As described below, stimulator unit 120 generates stimulation signals which are applied by contacts 148 to cochlea 140, thereby stimulating auditory nerve 114.

In certain embodiments, external coil 130 transmits electrical signals (i.e., power and stimulation data) to internal coil 136 via a radio frequency (RF) link, as noted above. Internal coil 136 is typically a wire antenna coil comprised of multiple turns of electrically insulated single-strand or multi-strand platinum or gold wire. The electrical insulation of internal coil 136 is provided by a flexible silicone molding (not shown). In use, implantable receiver unit 132 may be positioned in a recess of the temporal bone adjacent auricle 110 of the recipient.

There are several speech coding strategies that may be implemented by sound processing unit 126 to convert sound 103 into the encoded data signals. Embodiments of the present invention may be used in combination with any speech strategy now or later developed, including but not limited to Continuous Interleaved Sampling (CIS™), Spectral PEAK Extraction (SPEAK™), Advanced Combination Encoders (ACE™), Simultaneous Analog Stimulation (SAS), MPS, Paired Pulsatile Sampler (PPS), Quadruple Pulsatile Sampler (QPS), Hybrid Analog Pulsatile (HAPs), n-of-m and HiRes®, developed by Advanced Bionics. SPEAK™ is a low rate strategy that may operate within the 250-500 Hz range. ACE™ is a combination of CIS™ and SPEAK™. Examples of such speech strategies are described in U.S. Pat. No. 5,271,397, which is hereby incorporated by reference herein. The present invention may also be used with other speech coding strategies, such as a low rate strategy called Spread of Excitation which is described in U.S. Provisional No. 60/557,675 entitled, "Spread Excitation and MP3 coding Number from Compass UE" filed on Mar. 31, 2004, U.S. Provisional No. 60/616,216 entitled, "Spread of Excitation And Compressed Audible Speech Coding" filed on Oct. 7, 2004, and PCT Application WO 02/17679A1, entitled "Power Efficient Electrical Stimulation," which are hereby incorporated by reference herein. Certain embodiments of the present invention may be used on Cochlear Limited's Nucleus™ implant system that uses a range of coding strategies alternatives, including SPEAK™, ACE™, and CIS™. (HiRes is a registered trademark of Advanced Bionics Corporation, Sylmar, Calif., USA. SPEAK, ACE, and CIS are trademarks of Cochlear Limited, Lane Cove, NSW, Australia).

Embodiments of cochlear implant 100 may locally store several speech strategies, such as in the form of a software program or otherwise, any one of which may be selected depending, for example, on the aural environment. For example, a recipient may choose one strategy for a low noise environment, such as a conversation in an enclosed room, and a second strategy for a high noise environment, such as on a public street. The programmed speech strategies may be different versions of the same speech strategy, each programmed with different parameters or settings.

Figure 2B:
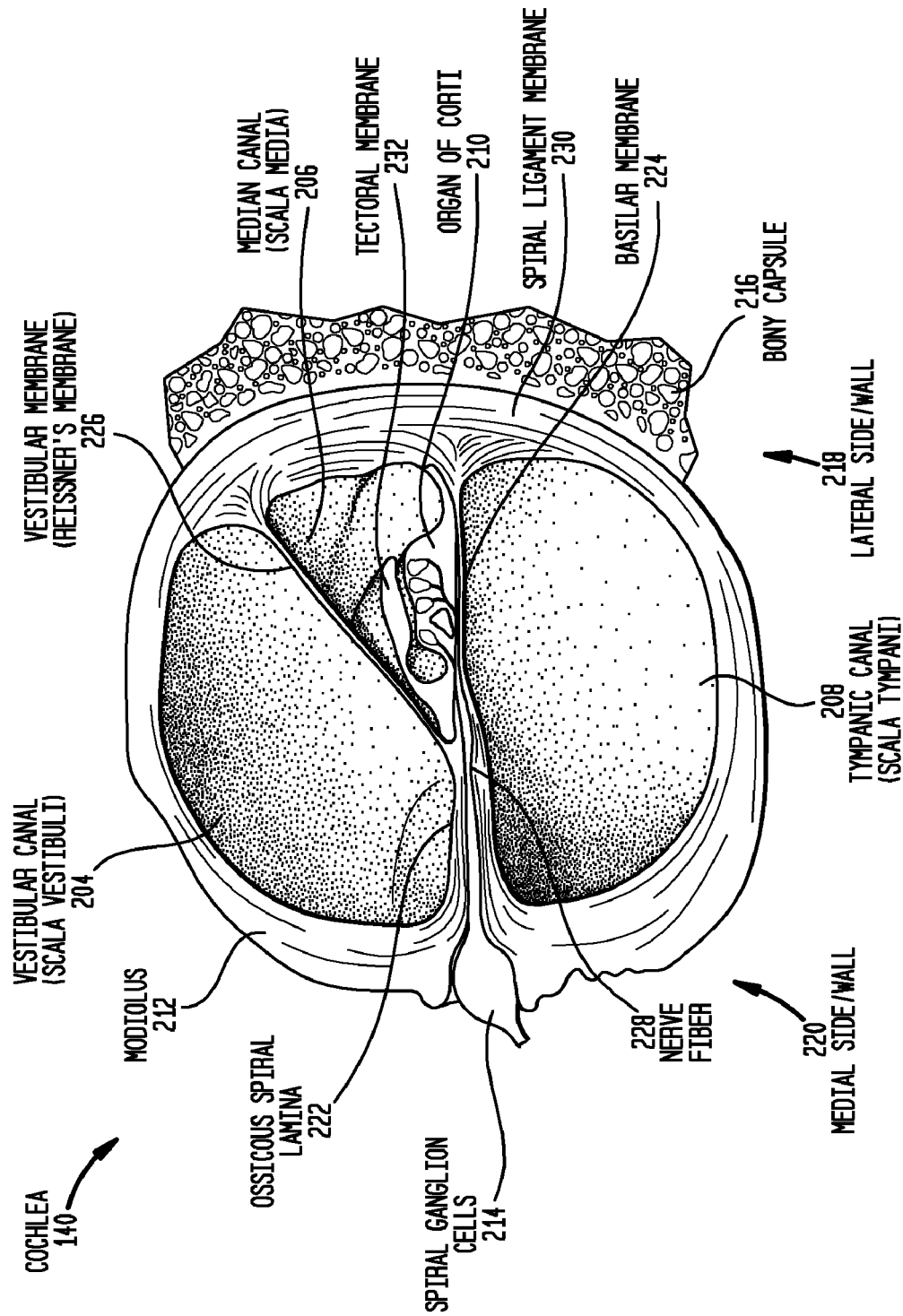
FIG. 2B is a cross-sectional view of one turn of the canals of a human cochlea.

Relevant aspects of cochlea 140 are described next below with reference to FIGS. 2A-2C. FIG. 2A is a perspective view of cochlea 140 partially cut-away to display the canals and nerve fibers of the cochlea. FIG. 2B is a cross-sectional view of one turn of the canals of cochlea 140. To facilitate understanding, the following description will reference the cochlea illustrated in FIGS. 2A and 2B as cochlea 140, which was introduced above with reference to FIG. 1.

Referring to FIG. 2A, cochlea 140 is a conical spiral structure comprising three parallel fluid-filled canals or ducts, collectively and generally referred to herein as canals 202. Canals 202 comprise the tympanic canal 208, also referred to as the scala tympani 208, the vestibular canal 204, also referred to as the scala vestibuli 204, and the median canal 206, also referred to as the scala media 206. Cochlea 140 has a conical shaped central axis, the modiolus 212, that forms the inner wall of scala vestibuli 204 and scala tympani 208. Tympanic and vestibular canals 208, 204 transmit pressure, while medial canal 206 contains the organ of corti 210 which detects pressure impulses and responds with electrical impulses which travel along auditory nerve 114 to the brain (not shown).

Cochlea 140 spirals about modiolus 212 several times and terminates at cochlea apex 134. Modiolus 212 is largest near its base where it corresponds to first turn 241 of cochlea 140. The size of modiolus 212 decreases in the regions corresponding to medial 242 and apical turns 246 of cochlea 140.

Referring now to FIG. 2B, separating canals 202 of cochlear 140 are various membranes and other tissue. The Ossicous spiral lamina 222 projects from modiolus 212 to separate scala vestibuli 204 from scala tympani 208. Toward lateral side 218 of scala tympani 208, a basilar membrane 224 separates scala tympani 208 from scala media 206. Similarly, toward lateral side 218 of scala vestibuli 204, a vestibular membrane 226, also referred to as the Reissner's membrane 226, separates scala vestibuli 204 from scala media 206.

Portions of cochlea 140 are encased in a bony capsule 216. Bony capsule 216 resides on lateral side 218 (the right side as illustrated in FIG. 2B), of cochlea 140. Spiral ganglion cells 214 reside on the opposing medial side 220 (the left side as illustrated in FIG. 2B) of cochlea 140. A spiral ligament membrane 230 is located between lateral side 218 of spiral tympani 208 and bony capsule 216, and between lateral side 218 of scala media 206 and bony capsule 216. Spiral ligament 230 also typically extends around at least a portion of lateral side 218 of scala vestibuli 204.

The fluid in tympanic and vestibular canals 208, 204, referred to as perilymph, has different properties than that of the fluid which fills scala media 206 and which surrounds organ of Corti 210, referred to as endolymph. Sound entering auricle 110 causes pressure changes in cochlea 140 to travel through the fluid-filled tympanic and vestibular canals 208, 204. As noted, organ of Corti 210 is situated on basilar membrane 224 in scala media 206. It contains rows of 16,000-20,000 hair cells (not shown) which protrude from its surface. Above them is the tectoral membrane 232 which moves in response to pressure variations in the fluid-filled tympanic and vestibular canals 208, 204. Small relative movements of the layers of membrane 232 are sufficient to cause the hair cells in the endolymph to move thereby causing the creation of a voltage pulse or action potential which travels along the associated nerve fiber 228. Nerve fibers 228, embedded within spiral lamina 222, connect the hair cells with the spiral ganglion cells 214 which form auditory nerve 114. Auditory nerve 114 relays the impulses to the auditory areas of the brain (not shown) for processing.

The place along basilar membrane 224 where maximum excitation of the hair cells occurs determines the perception of pitch and loudness according to the place theory. Due to this anatomical arrangement, cochlea 140 has characteristically been referred to as being "tonotopically mapped." That is, regions of cochlea 140 toward basal region 116 are responsive to high frequency signals, while regions of cochlea 140 toward apical end 116 are responsive to low frequency signals. These tonotopical properties of cochlea 140 are exploited in a cochlear implant by delivering stimulation signals within a predetermined frequency range to a region of the cochlea that is most sensitive to that particular frequency range.

Figure 3:
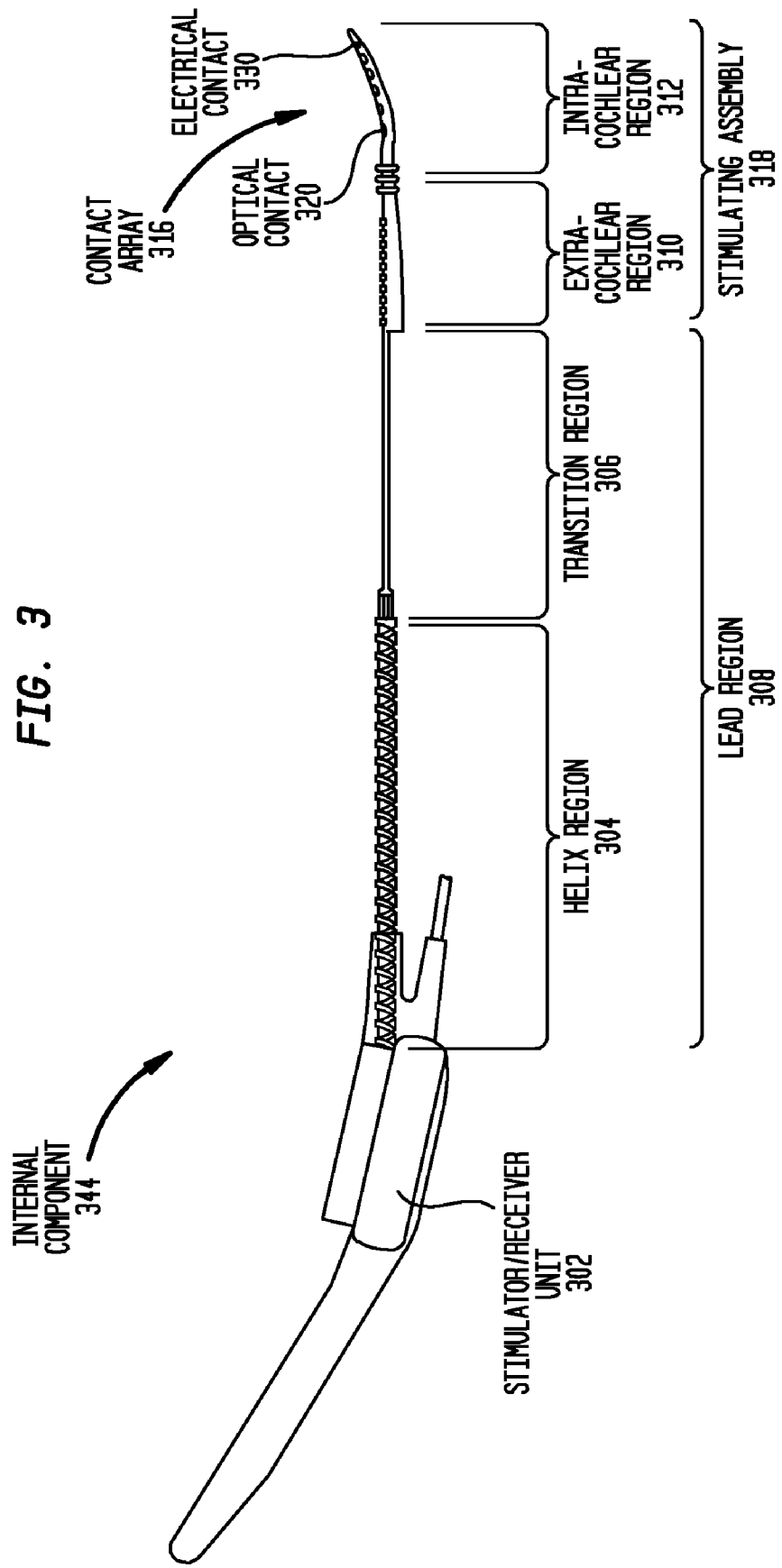
FIG. 3 is a side view of the implantable component of a cochlear implant in accordance with embodiments of the present invention.

FIG. 3 is a simplified side view of an embodiment of internal component 144, referred to herein as internal component 344. As shown in FIG. 3, internal component 344 comprises a stimulator/receiver unit 302 which, as described above, receives encoded signals from an external component of the cochlear implant. Internal component 344 terminates in a stimulating assembly 318 that comprises an extra-cochlear region 310 and an intra-cochlear region 312. Intra-cochlear region 312 is configured to be implanted in the recipient's cochlea and has disposed thereon an array 316 of contacts. In the illustrative embodiment of FIG. 3, contact array 316 comprises optical contacts 320 and electrical contacts 330. As described in greater detail below, contact array 316 may comprise any number of optical or electrical contacts 320, 330, in a variety of arrangements.

In certain embodiments, stimulating assembly 318 is configured to adopt a curved configuration during and or after implantation into the recipient's cochlea. To achieve this, in certain embodiments, stimulating assembly 318 is pre-curved to the same general curvature of a cochlea. Such embodiments of stimulating assembly 318, sometimes referred to as perimodiolar stimulating assemblies, are typically held straight by, for example, a stiffening stylet (not shown) which is removed during implantation so that the stimulating assembly may adopt its curved configuration when in the cochlea. Other methods of implantation, as well as other stimulating assemblies which adopt a curved configuration, may be used in alternative embodiments of the present invention.

In other embodiments, stimulating assembly 318 is a non-perimodiolar stimulating assembly which does not adopt a curved configuration. For example, stimulating assembly 318 may comprise a straight stimulating assembly or a mid-scala assembly which assumes a mid-scala position during or following implantation.

In certain embodiments, stimulator/receiver unit 302 may include one or more electromagnetic radiation (EMR) generators (not shown) and may include an electrical stimulation generator (also now shown) which generate optical and electrical stimulation signals, respectively, for application to the auditory nerve cells of the cochlear implant recipient. As described below, in other embodiments, the one or more EMR generators may be included in stimulating assembly 318.

Internal component 344 further comprises a lead region 308 coupling stimulator/receiver unit 302 to stimulating assembly 318. Lead region 308 comprises a helix region 304 and a transition region 306. Helix region 304 is a section of lead region 308 in which electrode leads are would helically. Transition region 306 connects helix region 304 to stimulating assembly 318. As described below, optical and/or electrical stimulation signals generated by stimulator/receiver unit 302 are delivered to contact array 316 via lead region 308. Helix region 304 prevents lead region 308 and its connection to stimulator/receiver 302 and stimulating assembly 318 from being damaged due to movement of internal component 144 which may occur, for example, during mastication.

FIG. 4 is a detailed functional block diagram illustrating the components of an embodiment of cochlear implant 100, referred to herein as cochlear implant 400. As shown, elements of cochlear implant 400 that have substantially the same or similar structures and/or performs substantially the same or similar functions as elements of cochlear implant 100 are illustrated in FIG. 4 using a 400 series reference number having two right digits which are the same as the right two digits as the corresponding element of FIG. 1. For example, as shown, cochlear implant 400 comprises an embodiment of external component 142 of FIG. 1, referred to as external component 442.

In the illustrative embodiment of FIG. 4, external component 442 comprises a behind-the-ear (BTE) device 434 and one or more sound input elements, such as microphone 424. BTE 434 is configured to be worn behind the ear of the recipient and, as described herein, may comprise various sound processing and other components. Microphone 424 may be positionable on BTE 434 or elsewhere on the recipient, and is configured to receive acoustic sound signals.

As would be appreciated by those of ordinary skill in the art, although the embodiments of FIG. 4 are described with reference to external component 442 configured as a BTE, other configurations of external component 442 may also be implemented in embodiments of the present invention. For example, in certain embodiments, external component 442 may be configured as a body-worn sound processing unit instead of, or in combination with, a component that is worn behind the ear. In other embodiments, external component 442 may be omitted and microphone 424 as well as the components residing in BTE device 434 may be implanted in the recipient. Such an arrangement of a cochlear implant is sometimes referred to as a totally-implantable cochlear implant. For ease of description, embodiments of the present invention will be primarily described herein with reference to cochlear implants having external components. However, embodiments of the present invention may be equally implemented in any cochlear implant now known or later developed.

As shown in FIG. 4, BTE device 434 comprises a sound processing unit 450, a transmitter 452 and a control module 454. As noted above, microphone 424 receives acoustic sound signals and delivers corresponding electrical signals to a preprocessor 432 of sound processing unit 450. Preprocessor 432 filters the electrical signals and delivers certain signals to an optical signal module 446 and certain signals to an electrical signal module 448. The filtering by preprocessor 432 may be based on a variety of factors including the frequency of the received signals, the current mode of operation of cochlear implant 400, or other criteria, at least some of which are specified to preprocessor 432 via control signals generated by control module 454. Optical signal module 446 performs signal processing operations on electrical signals received from preprocessor 432 into one or more encoded data signals 472 which are delivered to internal component 444 by transmitter 452. Electrical signal module 448 performs signal processing operations on the received signals to convert the electrical signals received from preprocessor 432 into one or more encoded data signals 474 which are also transmitted to internal component 444 by transmitter 452.

External component 442 may further comprise a control module 454. Control module 454 may be configured to receive control inputs from a recipient, an external device, or internally generated events, commands or interrupts. Control module 454 controls sound processing unit 450 and/or transmission of signals to internal component 444. As described below, in one embodiment, control module causes a control signal 475 to be transmitted to internal component 444.

In the embodiments illustrated in FIG. 4, cochlear implant 400 also includes an internal component 444 comprising a stimulator/receiver unit 402 and a stimulating assembly 418. Stimulator/receiver unit 402 comprises a receiver module 458 that receives from transmitter 452 encoded data signals 472, 474 and, in this illustrative embodiment, control signals 475. As shown, stimulator/receiver unit 402 includes an electromagnetic radiation (EMR) generator 462 that generates optical stimulation signals 463. Optical stimulation signals 463 are delivered to the recipient via optical contacts 420 of stimulating assembly 418. In certain embodiments, EMR generator 462 generates optical stimulation signals 463 based on encoded data signals 472. In other embodiments, EMR generator 462 generates optical stimulation signals 463 additionally or alternatively based on control signals 475. The application of optical stimulation signals 463 is described in greater detail below.

As shown, stimulator/receiver 402 also includes an electrical stimulation generator 460 that generates electrical stimulation signals 465 which are applied to the recipient via electrical contacts 430 of stimulating assembly 418. In some embodiments, electrical stimulation generator 460 generates electrical stimulation signals 465 based on encoded data signals 474. In other embodiments, electrical stimulator generator 460 generates electrical stimulation signals 465 additionally or alternatively based on one or more control signals 475 from control module 454. Stimulator/receiver unit 402 may generate optical stimulation signals 463 simultaneously or sequentially with electrical stimulation signals 465.

As noted, optical contacts 420 and electrical contacts 430 apply respective optical and electrical stimulation signals to the recipient. FIGS. 5A-5B and FIGS. 6A-6B are simplified side views of a distal portion of an elongate stimulating assembly 518 with combinations of optical and electrical contacts 520, 530 in accordance with embodiments of the present invention. The emission of energy is depicted with arrows 522, 524 and 532 in FIGS. 5A and 5B, and by arrows 622, 624 and 632 in FIGS. 6A and 6B. It should be appreciated that interpretation of the figures representing a given moment in time reflect embodiments of a cochlear implant that provide simultaneous stimulation; that is the emissions 522, 532 are emitted at the same time. Alternatively, interpretation of the figures representing no one moment in time reflects embodiments of a cochlear implant that provide sequential stimulation; that is, emissions 522 occurs prior to, or subsequent to, emission 532.

For ease of illustration, electrical contacts 530, 630, and optical contacts 520, 620, illustrated in FIGS. 5A-6B are shown in exemplary stimulating assemblies in an alternating arrangement. However, as described in greater detail below with reference to FIGS. 18A-18E, other arrangements may also be implemented.

As is well known to those of ordinary skill in the art, electrical stimulation signals travel though a biological medium in the direction in which the stimulation signals are emitted as well as in directions lateral to the intended direction of travel. This latter phenomenon is commonly referred to as the spread of excitation. For example, in the cochlea, applied electrical stimulation signals typically travel through the perilymph of the cochlea. This electrical stimulation signal stimulates the targeted nerve cells which are longitudinally aligned with and thus adjacent or proximate the emitting contact, while the spread of the electrical stimulation signal results in the stimulation of nerve cells which are positioned at various longitudinal distances from the emitting contact. This latter stimulation is referred to herein as dispersed electrical stimulation. The spread of an applied electrical stimulation signal may be affected by a variety of factors such as the intensity of the applied signal and the impedance of the medium through which the electrical stimulation signal propagates. For example, electrical stimulation signals may travel down a cochlea duct due to the low impedance of the cochlea perilymph. In contrast, the impedance of the nerve cells, other cochlea structures, as well as the surrounding bone and cartilage have a relatively higher impedance.

The spread of electrical stimulation signals may also be affected by the application of other electrical stimulation signals. For example, recent developments in electrical stimulation technology provide stimulating medical devices with the ability to provide electrical stimulation of only a spatially narrow or small region of nerve cells immediately adjacent or proximate the applying contact. This resulting pattern of stimulation is referred to as focused electrical stimulation. Some exemplary medical devices cause focused electrical stimulation through the interaction between two or more electrical stimulation signals. This interaction is described in commonly-owned and co-pending U.S. patent application Ser. No. 11/414,360, entitled "Focused Stimulation in a Medical Stimulation Device" and U.S. patent application Ser. No. 12/172,821, entitled "Use Of Focused Stimuli To Measure A Neural Excitation Profile Within The Cochlea," both of which are hereby incorporated by reference herein.

Optical stimulation signals generally travel in a relatively direct line and, as such, generally spread through a biological medium to a lesser extent than electrical stimulation signals. When applied, optical stimulation signals may cause stimulation of nerve cells adjacent or proximate the emitting contact, as well as nerve cells further along the direction of travel, such as nerve cells in an adjacent turn of the cochlea. Thus, in embodiments of the present invention, the spread of excitation caused by optical stimulation signals may be managed by the configuration of the optical contact. As such, in certain embodiments, the optical stimulation signals are applied in a manner which stimulates only a spatially narrow or small longitudinal region of nerve cells adjacent or proximate to the emitting optical contact. This resulting pattern of stimulation is referred to herein as focused optical stimulation. In other embodiments, optical stimulation signals are applied to stimulate nerve cells positioned at relatively greater longitudinal distances from the emitting optical contact. This resulting pattern of stimulation is referred to herein as dispersed optical stimulation.

As would be appreciated by one or ordinary skill in the art, the spread of an applied optical stimulation signal may also be affected by the intensity of the stimulation, the degree to which the optical stimulation signal is dispersed or focused, and the medium through which the optical stimulation signal propagates. For example, in accordance with certain embodiments of the present invention, the configuration of optical contacts 520 may determine the direction of travel of an optical stimulation signal and/or the spread of the signal from the contact. The configuration of the optical stimulation contacts is described in further detail below.

Referring to FIG. 5A, a distal portion 516 of an embodiment of stimulating assembly 118, referred to herein as stimulating assembly 518 is shown. Distal portion 516 comprises a plurality of longitudinally arranged electrical contacts 530 and optical contacts 520. As shown, contacts 520 and 530 are spaced from one another along the length of stimulating assembly 518. For ease of illustration, electrical contacts 530 are depicted as rectangles and optical contacts 520 are depicted as ovals. These exemplary shapes are provided only to facilitate understanding of embodiments of the present invention and do not define or limit electrical contacts 530 or optical contacts 520 in any manner.

In the embodiment of FIG. 5A, optical contact 520 is configured and/or oriented such that applied optical stimulation signals 522 are dispersed, resulting in dispersed optical stimulation 509 of cochlea tissue 531. Furthermore, in the illustrative embodiments of FIG. 5A, electrical contact 530 is configured and/or oriented such that applied electrical stimulation signals 532 are dispersed, resulting in dispersed electrical stimulation 507 of cochlea tissue 531.

In the embodiments illustrated in FIG. 5B, optical contact 520 is configured and/or oriented such that applied optical stimulation signals 524 are substantially focused, resulting in focused optical stimulation 511 of cochlea tissue 531. Furthermore, in the illustrative embodiments of FIG. 5B, electrical contact 530 is configured and/or oriented such that applied electrical stimulation signals 532 are dispersed, resulting in dispersed electrical stimulation 507 of cochlea tissue 531.

Figure 5C:
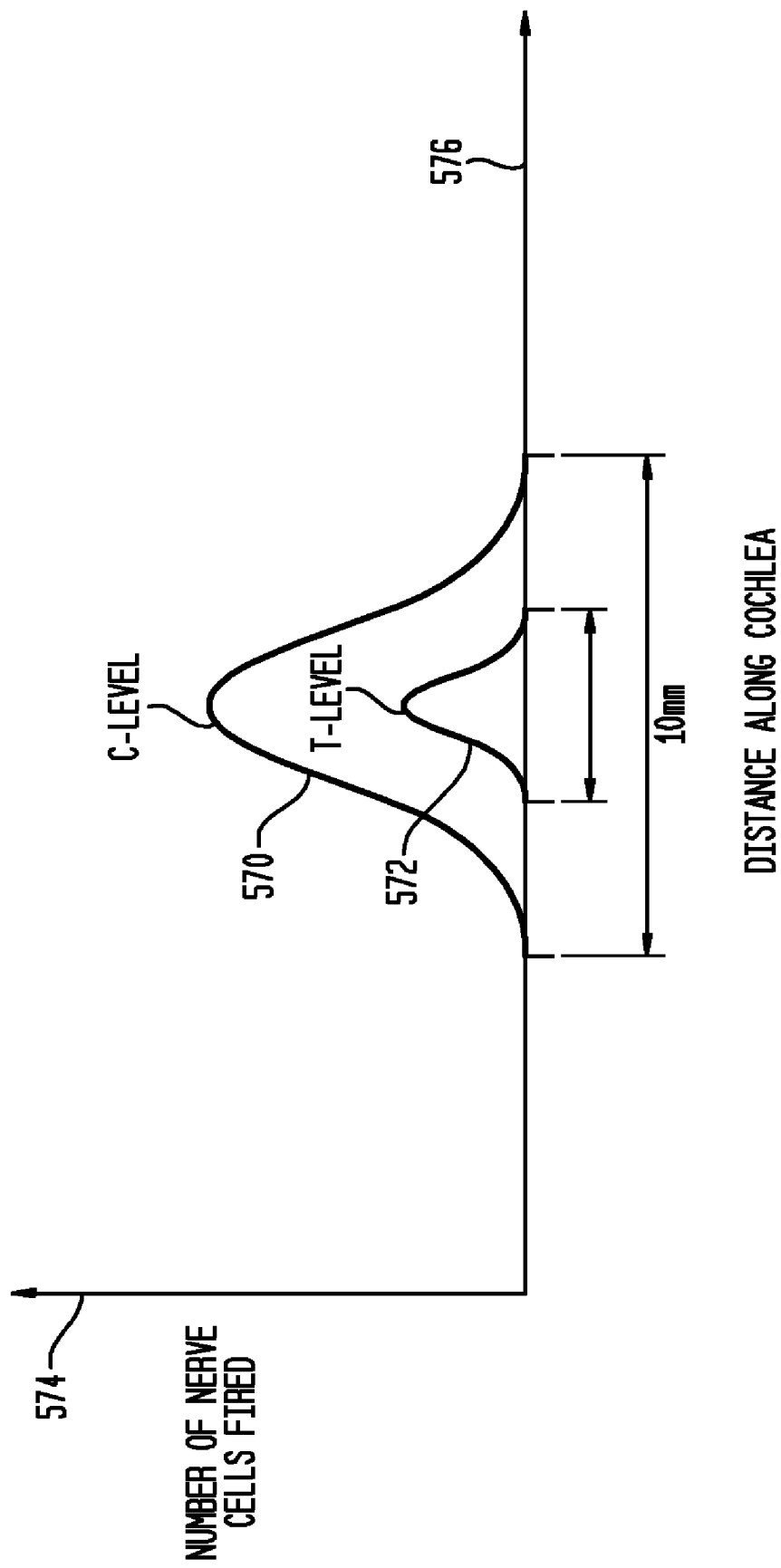
FIG. 5C is a graph illustrating the spread of electrical stimulation along a recipient's cochlea.

As noted, in certain embodiments of the present invention electrical stimulation signals delivered to a recipient's cochlea will result in dispersed stimulation of the cochlea (i.e. stimulation of nerve cells adjacent or proximate the electrical contact, as well as nerve cells positioned at various distances from the contact). FIG. 5C is a graph illustrating two exemplary dispersed stimulation patterns resulting from the delivery of electrical stimulation signals to a recipient's cochlea. As discussed in greater detail below with reference to FIG. 7, delivery of electrical stimulation signals to a recipient's cochlea causes nerve cells along the cochlea to fire, thereby generating an action potential which is transmitted along the auditory pathway. As such, the graph in FIG. 5C illustrates dispersed stimulation patterns in terms of the number of nerve cells which are fired, illustrated as axis 574, at various distances along the cochlea from a point of stimulation. As shown, the point of stimulation is the region of the cochlea where the greatest number of nerve cells are fired, and the distance along the cochlea is shown as axis 576.

FIG. 5C illustrates a first spread pattern 572 resulting from the delivery of an electrical stimulation signal at the recipient's threshold level (T-Level). In the illustrative embodiment, the recipient's T-Level is 0.4 mA, and the electrical stimulation signal is applied for 25 microseconds. Therefore, when 0.4 mA of current is applied for 25 microseconds, the spread of electrical stimulation is illustrated by pattern 572. As shown, the number of nerve cells fired decreases as the distance from the point of stimulation increases.

FIG. 5C also illustrates a second spread pattern 570 resulting from the delivery of an electrical stimulation signal at the recipient's comfort level (C-Level). In the illustrative embodiment, the recipient's C-Level is twice the recipient's T-Level, or 0.8 mA, and the electrical stimulation signal is again applied for 25 microseconds. Therefore, when 0.8 mA of current is applied for 25 microseconds, the spread of electrical stimulation is illustrated by pattern 570. As shown, the number of nerve cells fired decreases as the distance from the point of stimulation increases.

In FIG. 5C, pattern 570 has an approximate width of 10 mm. As such, nerve cells approximately 5 mm on either side of the point of stimulation are fired. It would be appreciated by one of ordinary skill in the art that the T-Level, C-Level, current levels and times are merely illustrative, and should not be construed to limit embodiments of the present invention.

FIG. 6A illustrates a distal portion 616 of an embodiment of stimulating assembly 618, referred to herein as stimulating assembly 618. Similar to stimulating assembly 518 described above with reference to FIGS. 5A and 5B, stimulating assembly 618 comprises a plurality of longitudinally arranged electrical contacts 630 and optical contacts 620.

In the embodiment of FIG. 6A, optical contact 620 is configured and/or oriented such that applied optical stimulation signals 622 are dispersed, resulting in dispersed optical stimulation 609 of cochlea tissue 631. Furthermore, in the illustrative embodiments of FIG. 6A, electrical contact 630 is configured and/or oriented such that applied electrical stimulation signals 632 are substantially focused, resulting in focused electrical stimulation 607 of cochlea tissue 631.

In the embodiments illustrated in FIG. 6B, optical contact 620 is configured and/or oriented such that applied optical stimulation signals 624 are substantially focused, resulting in focused optical stimulation 611 of cochlea tissue 631. Furthermore, in the illustrative embodiments of FIG. 6B, electrical contact 630 is configured and/or oriented such that applied electrical stimulation signals 632 are substantially focused, resulting in focused electrical stimulation 607 of cochlea tissue 631.

The embodiments described with reference to FIGS. 5A-6B above have been provided for illustrative purposes only. It would be appreciated that the various embodiments described above may be combined or otherwise altered to fit the needs of the recipient or the cochlear implant. For example, in certain embodiments of FIG. 6A, an optical stimulation signal 622 applied via a first optical contact 620A may cause dispersed optical stimulation, while an optical stimulation signal (not shown) delivered to a second optical contact 620B may cause focused optical stimulation. Similarly, in other embodiments of FIG. 6A, an electrical stimulation signal 632 applied via a first electrical contact 630A may cause focused electrical stimulation, while an electrical stimulation signal delivered to a second electrical contact 630B may cause dispersed electrical stimulation. As would be appreciated, all various combinations of optical and electrical stimulation are within the scope of the present invention.

As is well known in the art, the human auditory system is composed of many structural components, some of which are connected extensively by bundles of nerve cells (neurons). Each nerve cell has a cell membrane which acts as a barrier to prevent intercellular fluid from mixing with extracellular fluid. The intercellular and extracellular fluids have different concentrations of ions, which leads to a difference in charge between the fluids. This difference in charge across the cell membrane is referred to herein as the membrane potential (Vm) of the nerve cell. Nerve cells use membrane potentials to transmit signals between different parts of the auditory system.

In nerve cells that are at rest (i.e., not transmitting a nerve signal) the membrane potential is referred to as the resting potential of the nerve cell. Upon receipt of a stimulus, the electrical properties of a nerve cell membrane are subjected to abrupt changes, referred to herein as a nerve action potential, or simply action potential. The action potential represents the transient depolarization and repolarization of the nerve cell membrane. The action potential causes electrical signal transmission along the conductive core (axon) of a nerve cell. Signals may be then transmitted along a group of nerve cells via such propagating action potentials.

FIG. 7 is graph illustrating the various phases of an idealized action potential 702 as the potential passes through a nerve cell in accordance with embodiments of the present invention. The action potential is presented as membrane voltage in millivolts (mV) versus time. As would be appreciated by one of ordinary skill in the art, the membrane voltages and times shown in FIG. 7 are provided for illustration purposes only. The actually voltages may vary depending on the individual. As such, this illustrative example should not be construed as limiting the present invention.

In the example of FIG. 7, prior to application of a stimulus 718 to the nerve cell, the resting potential of the nerve cell is approximately −70 mV. Stimulus 718 is applied at a first time. In normal hearing, this stimulus is provided by movement of the hair cells of the cochlea. Movement of these hair cells results in the release of a nerve impulse, sometimes referred to as neurotransmitter. In embodiments of the present invention, the stimulus is the result of the application of optical and/or electrical stimulation signals to the nerve cells.

As shown in FIG. 7, following application of stimulus 718, the nerve cell begins to depolarize. Depolarization of the nerve cell refers to the fact that the voltage of the cell becomes more positive following stimulus 718. When the membrane of the nerve cell becomes depolarized beyond the cell's critical threshold, the nerve cell undergoes an action potential. This action potential is sometimes referred to as the "firing" of the nerve cell. As used herein, the critical threshold of a nerve cell, group of nerve cells, etc. refers to the threshold level at which the nerve cell, group of nerve cells, etc. will undergo an action potential. In the example illustrated in FIG. 7, the critical threshold level for firing of the nerve cell is approximately −50 mV. As would be appreciated, the critical threshold and other transitions may be different for various recipients. As such, the values provided in FIG. 7 are merely illustrative. For consistency, a critical threshold of −50 mV will be used herein, but such usage should not be considered to limit the present invention The course of this action potential in the nerve cell can be generally divided into five phases. These five phases are shown in FIG. 7 as a rising phase 704, a peak phase 705, a falling phase 706, an undershoot phase 714, and finally a refractory period 717. During rising phase 704, the membrane voltage continues to depolarize. The point at which depolarization ceases is shown as peak phase 705. In the illustrative embodiment of FIG. 7, at this peak phase 705, the membrane voltage reaches a maximum value of approximately 40 mV.

Following peak phase 705, the action potential underfoes falling phase 706. During falling phase 706, the membrane voltage becomes increasingly more negative, sometimes referred to as hyperpolarization of the nerve cell. This hyperpolarization causes the membrane voltage to temporarily become more negatively charged then when the nerve cell is at rest. This phase is referred to as the undershoot phase 714 of action potential 702. Following this undershoot, there is a time period during which it is impossible or difficult for the nerve cells to fire. This time period is referred to as refractory period 717.

Action potential 702 illustrated in FIG. 7 may travel along, for example the auditory nerve, without diminishing or fading out because the action potential is regenerated each nerve cell. This regeneration occurs because an action potential at one nerve cell raises the voltage at adjacent nerve cells. This induced rise in voltage depolarizes adjacent nerve cells thereby provoking a new action potential therein.

As noted above, the nerve cell must obtain a membrane voltage above a critical threshold before the nerve cell may fire. Illustrated in FIG. 7 are several failed initiations 716 which occur as a result of stimuli which were insufficient to raise the membrane voltage above the critical threshold value to result in an action potential.

In normal hearing there is a level of spontaneous or random nerve activity in the absence of sound that is inaudible to an individual. This spontaneous nerve activity is the result of the random release of neurotransmitters by the cochlea hair cells. When a neurotransmitter is randomly released (in the absence of sound), the neurotransmitter causes the spontaneous firing of an auditory nerve cell. Many of these combine to cause a level of inherent background noise. However, in cochlear implant recipients and other individuals, such as individuals suffering from tinnitus, this spontaneous nerve activity is lacking.

One aspect of the present invention is directed to invoking stochastic or random activity within a nerve cell, referred to as pseudospontaneous nerve activity, through the application of one or more optical stimulation signals to the nerve cells. In certain embodiments, this pseudospontaneous nerve activity replicates the spontaneous or random nerve activity experienced by individuals with normal hearing. By replicating the naturally occurring spontaneous activity cochlear implants may provide stimulated hearing that more closely replicates natural hearing. This may advantageously facilitate more accurate speech perceptions and/or the suppression of tinnitus. In certain embodiments of the present invention, the intensity of the optical stimulation signals which encourage, facilitate or allow the pseudospontaneous nerve activity is below the recipient's perception or auditory threshold.

FIG. 8 is two graphs showing nerve activity for a given membrane voltage. Graph 801 illustrates membrane voltage of a nerve cell prior to, and during the application of an optical stimulation signal configured to encourage, facilitate or allow pseudospontaneous nerve activity. Graph 803 illustrates the corresponding random nerve firing caused by internal metabolic activity.

Referring to graph 801, the resting potential 802 of a nerve cell is approximately −70 mV. At a first time, an optical stimulation signal is applied to the recipient's cochlea to depolarize the nerve cells. The optical stimulation signal has an intensity which depolarizes the nerve cells to slightly below the critical threshold 807 which, in the embodiment of FIG. 8, is approximately −50 mV. As noted above, once the membrane voltage increases to this level, the nerve cells may fire randomly as a result of the internal metabolic nerve activity within the nerve cells.

Graph 803 includes a number of spikes 805 illustrating the pseudospontaneous nerve activity which occurs while the nerve cells have a membrane voltage above the critical threshold. Each spike indicates a firing of a nerve cell. As shown, these firings occur at random or at least semi-random times following application of the optical stimulation signal.

Electrical stimulation signals generally include a positive pulse followed by a negative pulse. The positive pulse depolarizes the nerve cells, while the negative pulse hyperpolarizes the nerve cells, thereby providing charge recovery and eliminating the depolarization. This charge recovery prevents generation of toxic electrochemical by-products in the cochlea as well as prevents damage to an electrical contact which would be caused by multiple pulses having the same polarity.

In contrast, electromagnetic (EM) radiation does not generate toxic by-products within the cochlea. As such, charge recovery utilized in electrical stimulation is not required. As such, an optical stimulation signal may comprise a pulse of EM radiation of any time duration.

FIG. 9 is two graphs illustrating exemplary optical and electrical stimulation signals that may be applied to a recipient's nerve cells. An optical stimulation signal 902, shown in graph 901, is applied at an intensity 931 which depolarizes the nerve cells to less than or up to the critical threshold. As shown, optical stimulation signal 902 comprises a pulse of electromagnetic (EM) radiation which is applied at a first time. The EM radiation is continuously applied for some period of time. Because the nerve cells are depolarized to or near the critical threshold, pseudospontaneous nerve activity occurs in the nerve cells.

Graph 903 illustrates electrical stimulation signals 904. Stimulation signals 904 represent one or more frequency components of a sound signal and are delivered to a recipient's cochlea 140 (FIG. 1) at an intensity 933 to evoke a hearing percept by the recipient of the one or more frequency components. In the illustrative embodiment of FIG. 9, electrical stimulation signals 904 are applied concurrently with optical stimulation signal 902 to different nerve populations.

As noted above, in normal hearing, spontaneous nerve activity occurs in the absence of sound. However, such spontaneous nerve activity also occurs prior to, during or subsequent to perception of a sound in normal hearing. This spontaneous nerve activity enhances the sound perception by more closely replicating natural hearing. Because electrical stimulation signals 904 are delivered concurrently with optical stimulation signal 902 to encourage, facilitate or allow internal metabolic activity to cause pseudospontaneous nerve activity, the recipient may experience a hearing percept which is superior to that provided by conventional cochlear implants.

As noted, the embodiments illustrated in FIG. 9 are merely illustrative and should not be considered to limit the scope of the present invention. For example, in alternative embodiments, electrical stimulation signals 904 may be applied prior to, or subsequent to application of optical stimulation signals 902.

As would be appreciated by one of ordinary skill in the art, optical and electrical stimulation signals may be delivered to the same or different populations. In the illustrative embodiments of FIG. 9, the signals are delivered to different nerve cell populations which, as described above, enhances the sound perception. In alternative embodiments in which the optical and electrical signals are delivered to the same nerve cell populations, the optical and electrical signals may be delivered at different times to avoid overstimulation of the nerve cells.

FIG. 10A is a high level flowchart illustrating operations that may be performed to stimulate the nerve cells of a recipient in accordance with embodiments of the present invention. The stimulation process begins at block 1002. At block 1004, one or more optical stimulation signals are applied to the recipient's nerve cells at a duration and intensity to encourage, facilitate or allow pseudospontaneous nerve activity. The stimulation process then ends at block 1008.

Figure 10B:
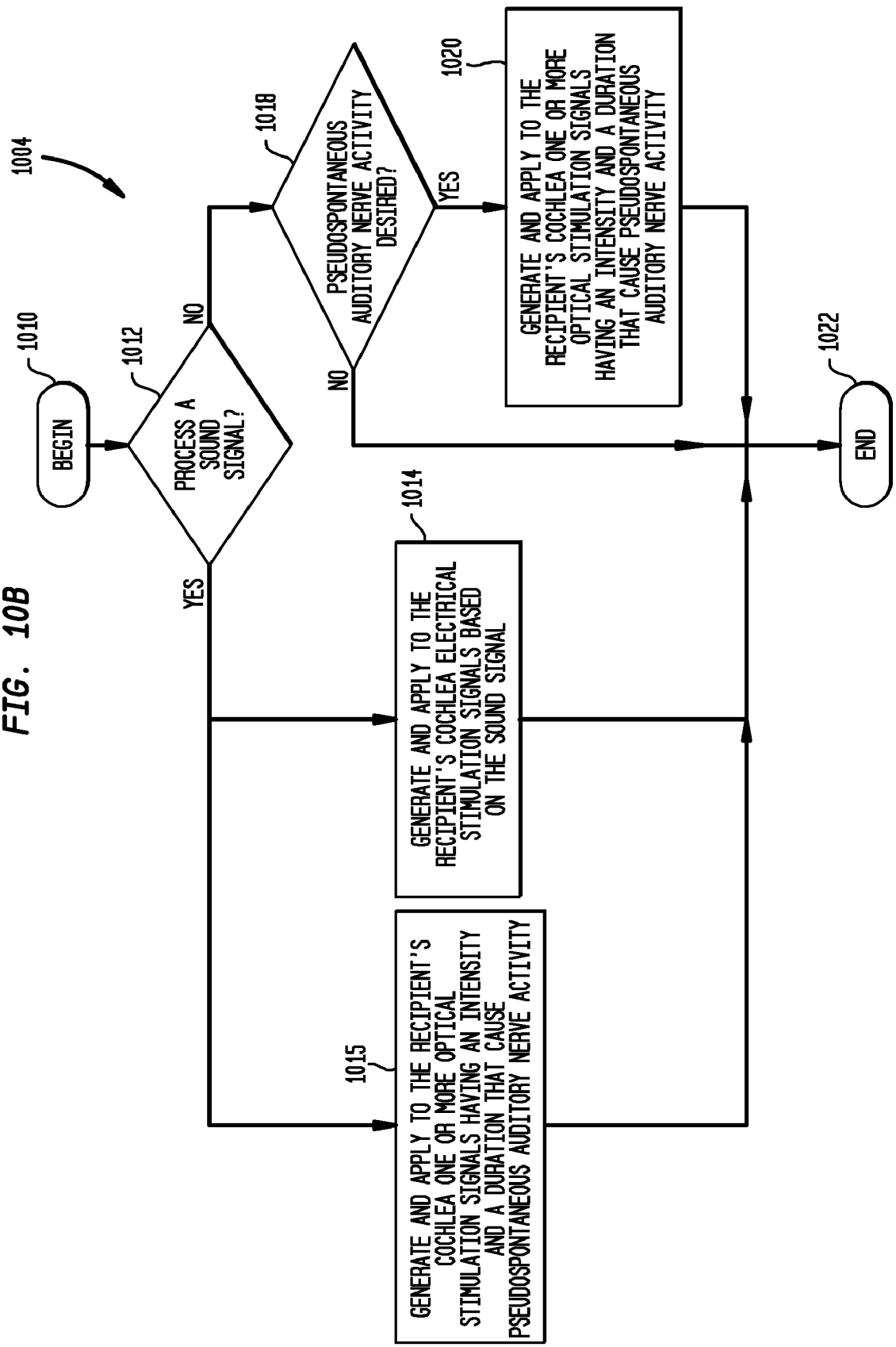
FIG. 10B is a detail level flowchart illustrating operations that may be performed in a cochlear implant in accordance with certain embodiments of the present invention.

FIG. 10B is a detailed flowchart illustrating the operations that may be performed in accordance with embodiments of block 1004 of FIG. 10A. The operations begin at block 1010. At block 1012, a decision is made if a sound signal has been received and/or whether the signal should be processed. If a received sound signal is to be processed, the method progresses to blocks 1014 and 1015. At block 1015, one or more optical stimulation signals are generated and applied to the recipient's nerve cells at an intensity and duration that to encourage, facilitate or allow pseudospontaneous nerve activity. At block 1014, electrical stimulation signals based on the received sound signal are generated and applied to the recipient's nerve cells. The operations of blocks 1015 and 1014 may occur sequentially or concurrently. The operations then end at block 1022.

Returning to block 1012, if no sound signal is to be processed, the method progresses to block 1018. A block 1018 a determination is made as to whether pseudospontaneous auditory nerve activity is desired. If pseudospontaneous auditory nerve activity is not desired, the method ends at block 1022. However, if pseudospontaneous auditory nerve activity is desired, the method continues to block 1020. At block 1020, one or more optical stimulation signals are generated and applied to the recipient's nerve cells at an intensity and duration to encourage, facilitate or allow pseudospontaneous auditory nerve activity. The method then ends at block 1022.

It would be appreciated that the embodiments illustrated in FIGS. 10A and 10B are merely illustrative and should not be considered to limit the scope of the present invention.

As noted above, described aspects of the present invention are generally directed to optically stimulating a recipient's nerve cells to encourage, facilitate or allow pseudospontaneous nerve activity. Other aspects of the present invention are generally directed to delivering combinations of optical and electrical stimulation signals to a recipient's nerve cells to increase neural survival. For example, cochlear nerve cells which are not used to receive a hearing percept will eventually become non-functional. In other words, used spiral ganglion or other cells will die and thus loss the ability to transmit electrical potentials. Certain aspects of the present invention are directed to increasing the neural survival rate of such unused cochlear nerve cells in a cochlear implant recipient. In these aspects, the nerve cells are stimulated to evoke a hearing percept, and nerve cells which are not used to perceive a sound are sequentially or concurrently stimulated to maintain substantial neural survival of those cells. These aspects of the present invention may use the same cochlear implant as shown above in FIGS. 1, 3 and 4.

FIG. 11A illustrates optical and electrical stimulation signals 1102, 1103 that may be applied to a recipient's cochlea 140 (FIG. 1). In graph 1101, optical stimulation signals 1102 are generated based on a received sound signal. Optical stimulation signals 1102 are applied to cochlea 140 at an intensity 1131 that exceeds the recipient's auditory threshold, thereby evoking a hearing percept. As would also be appreciated, the duration, frequency and intensity of the optical stimulation signals may depend on the received sound, the sound processing strategy used, the needs of the recipient, etc.

As shown in graph 1103, electrical stimulation signals 1104 are applied to cochlea 140 following application of optical stimulation signals 1102. Electrical stimulation signals 1104 are generated and applied to cochlea 140 at an intensity 1133 to maintain substantial neural survival of the nerve cells. Intensity 1133 is preferably below the recipient's auditory threshold. As would be appreciated, the intensity and/or frequency of the electrical stimulation signals may depend on the needs of the recipient.

FIG. 11B illustrates optical and electrical stimulation signals 1106, 1108, that may be applied to cochlea 140. In graph 1105, optical stimulation signals 1006 are generated based on a received sound signal. Optical stimulation signals 1106 are applied at an intensity 1135 that evokes a hearing percept by the recipient. In graph 1107, electrical stimulation signals 1108 are applied at an intensity 1137 to maintain neural survival. As shown, a first set 1110 of electrical stimulation signals 1108 is delivered concurrently with optical stimulation signals 1106 while a second set 1112 of electrical stimulation signals 1108 is applied following application of optical stimulation signals 1106.

As would be appreciated by one of ordinary skill in the art, FIGS. 11A and 11B illustrated specific examples of the embodiments described above. In certain embodiments, there is a likelihood that there is an overlap of the optical and electrical stimulation signals on the same nerve cell population. In such embodiments, the intensities of the signals would be moderated to prevent overstimulation of the nerve cell population. This may be implemented, for example, by a time delay or reducing the signal intensity of one or more signals.

FIG. 12 is a flowchart illustrating a method 1201 performed during operation of cochlear implant 100. Method 1201 may be performed continually or periodically during operation. Illustrative method 1201 begins at block 1216. At block 1218 a decision is made as to whether a sound signal has been received and is to be processed. If the received sound signal is to be processed, the method progresses to block 1222.

At block 1222, a decision is made as to whether neural-survival stimulation is also desired based on, for example, a user input, a pre-programmed process, etc. If neural survival stimulation is not desired, optical stimulation signals are generated based on the received sound signal and are applied to cochlea 140 (FIG. 1) at block 1226. However, if neural survival stimulation is desired, the method continues to block 1223. That is, if cochlear implant 100 determines that stimulation signals to evoke a hearing percept of the received sound signal, and neural survival stimulation signals should be applied to cochlea 140, the method progresses to block 1223. At block 1223, optical stimulation signals are generated based on the received sound signal, and are applied to the recipient's cochlea. Also at block 1223, electrical stimulation signals configured to maintain neural survival are generated and applied to the recipient's cochlea. The method then ends at block 1234.

Returning to block 1218, if a received sound signal is not to be processed, the method progresses to block 1228. That is, if cochlear implant 100 determines that no sound signal has been received, or at that a received sound signal is not to be processed, the method progresses to block 1228. At block 1228, a decision is made as to whether neural-survival stimulation is desired. If neural survival stimulation is not desired, the method ends at block 1234. However, if neural survival stimulation is desired, the method continues to block 1230. At block 1230, electrical stimulation signals configured to maintain neural survival are generated and applied to the recipient's cochlea. The method then ends at block 1234.

As noted above, FIGS. 11A-12 illustrate embodiments of the present invention in which optical stimulation signals are used to evoke a hearing perception, and in which electrical stimulation signals are used to maintain substantial neural survival. FIGS. 13A-14 illustrate alternative embodiments of the present invention in which electrical stimulation signals are used to evoke a hearing percept and optical stimulation signals are used to maintain neural survival.

FIG. 13A illustrates optical and electrical stimulation signals that may be applied to a recipient's cochlea 140 (FIG. 1) in accordance with embodiments of the present invention. In graph 1303, electrical stimulation signals 1304 are generated based on a received sound signal and applied to cochlea 140 at an intensity 1331 to evoke a hearing percept. As would be appreciated, the duration, frequency and intensity of the electrical stimulation signals may depend on the received sound, the sound processing strategy used, the needs of the recipient, etc. In graph 1303, following application of electrical stimulation signals 1304, optical stimulation signals 1302 are applied to cochlea 140 at an intensity 133 to maintain neural survival. These neural-survival stimulation signals have an intensity which is below the auditory threshold of the recipient. As would be appreciated, the intensity and/or frequency of the optical stimulation signals may depend on the needs of the recipient.

FIG. 13B illustrates other optical and electrical stimulation signals that may be applied to cochlea 140 in accordance with embodiments of the present invention. In graph 1305, optical stimulation signals 1108 are generated and applied to cochlea 140 to maintain neural survival. In graph 1307, electrical stimulation signals 1308 are generated and applied to cochlea 140 based on a received sound signal to evoke a hearing percept. As shown, optical stimulation signals 1306 are delivered concurrently with electrical stimulation signals 1308.

FIG. 13C still another exemplary optical and electrical stimulation signals that may be applied to cochlea 140. In graph 1311, electrical stimulation signals 1312 are generated and applied to the recipient's cochlea based on a received sound signal to evoke a hearing percept. In graph 1305, an optical stimulation signal 1310 is concurrently generated and applied to the recipient's cochlea to maintain neural survival.

FIG. 14 is a flowchart illustrating a method 1401 performed during operation of cochlear implant 100. Method 1401 may be performed continually or periodically during operation. Illustrative method 1401 begins at block 1416. At block 1418 a decision is made as to whether a sound signal has been received and is to be processed. If the received sound signal is to be processed, the method progresses to block 1422.

At block 1422, a decision is made as to whether neural-survival stimulation is also desired based on, for example, a user input, a pre-programmed process, etc. If neural survival stimulation is not desired, electrical stimulation signals are generated based on the received sound signal and are applied to cochlea 140 (FIG. 1) at block 1426. However, if neural survival stimulation is desired, the method continues to block 1423. That is, if cochlear implant 100 determines that stimulation signals to evoke a hearing percept of the received sound signal, and neural survival stimulation signals should be applied to cochlea 140, the method progresses to block 1423. At block 1423, electrical stimulation signals are generated based on the received sound signal, and are applied to the recipient's cochlea. Also at block 1423, optical stimulation signals configured to maintain neural survival are generated and applied to cochlea 140. The method then ends at block 1434.

Returning to block 1418, if a received sound signal is not to be processed, the method progresses to block 1428. That is, if cochlear implant 100 determines that no sound signal has been received, or at that a received sound signal is not to be processed, the method progresses to block 1428. At block 1428, a decision is made as to whether neural-survival stimulation is desired. If neural survival stimulation is not desired, the method ends at block 1434. However, if neural survival stimulation is desired, the method continues to block 1430. At block 1430, electrical stimulation signals configured to maintain neural survival are generated and applied to the recipient's cochlea. The method then ends at block 1434.

It would be appreciated that the above described embodiments are merely provided for illustration purposes, and the neural-survival stimulation parameters such as frequency, timing, location, etc. may vary. For example, the various characteristics of the neural-survival stimulation signals may be controlled by, for example, a control module, such as the control module described above with reference to FIG. 4. In some embodiments, the control module may cause the cochlear implant to generate the electrical stimulation signals only when optical stimulation signals have not been delivered for a period of time. In still other embodiments, the electrical stimulation signals may be generated when the cochlear implant enters a predetermined mode of operation, or device state, such as, for example, a sleep mode of operation.

In the aspects of the present invention described with reference to FIGS. 11A-14, stimulation signals configured to evoke a hearing percept are generated and applied to a recipient's cochlea 140 (FIG. 1) in combination with stimulation signals configured to maintain substantial neural survival. In other aspects of the present invention, optical stimulation signals are concurrently delivered to a region of the recipient's cochlea in order to reduce the intensity of electrical stimulation required to evoke a hearing percept during stimulated hearing. These aspects of the present invention may use the same cochlear implant as shown above in FIGS. 1, 3 and 4.

In conventional electrically-stimulating cochlear implants, electrical stimulation signals must have a minimum intensity in order to evoke a hearing percept. Specifically, the electrical stimulation signals must have an intensity which increases the membrane voltage of the cells from the resting level (resting potential) to a level at which the nerve cells will fire. The minimum required intensity is referred to herein as a recipient's auditory threshold level. Embodiments of the present invention reduce this required intensity by applying an optical stimulation signal to the recipient's auditory nerve cells prior to and during application of electrical stimulation signals. The optical stimulation signal has an intensity which increases the membrane voltage of the nerve cells to less than or equal to approximately the recipient's critical threshold. As described above with reference to FIG. 7, nerve cells having a membrane voltage at or near the recipient's critical threshold will fire more readily than cells having a membrane voltage at the resting potential. Therefore, because the nerve cells will fire more readily, electrical stimulation signals having an intensity below the recipient's auditory threshold level will cause the optically stimulated nerve cells to fire, thereby evoking a hearing percept.

Figure 15:
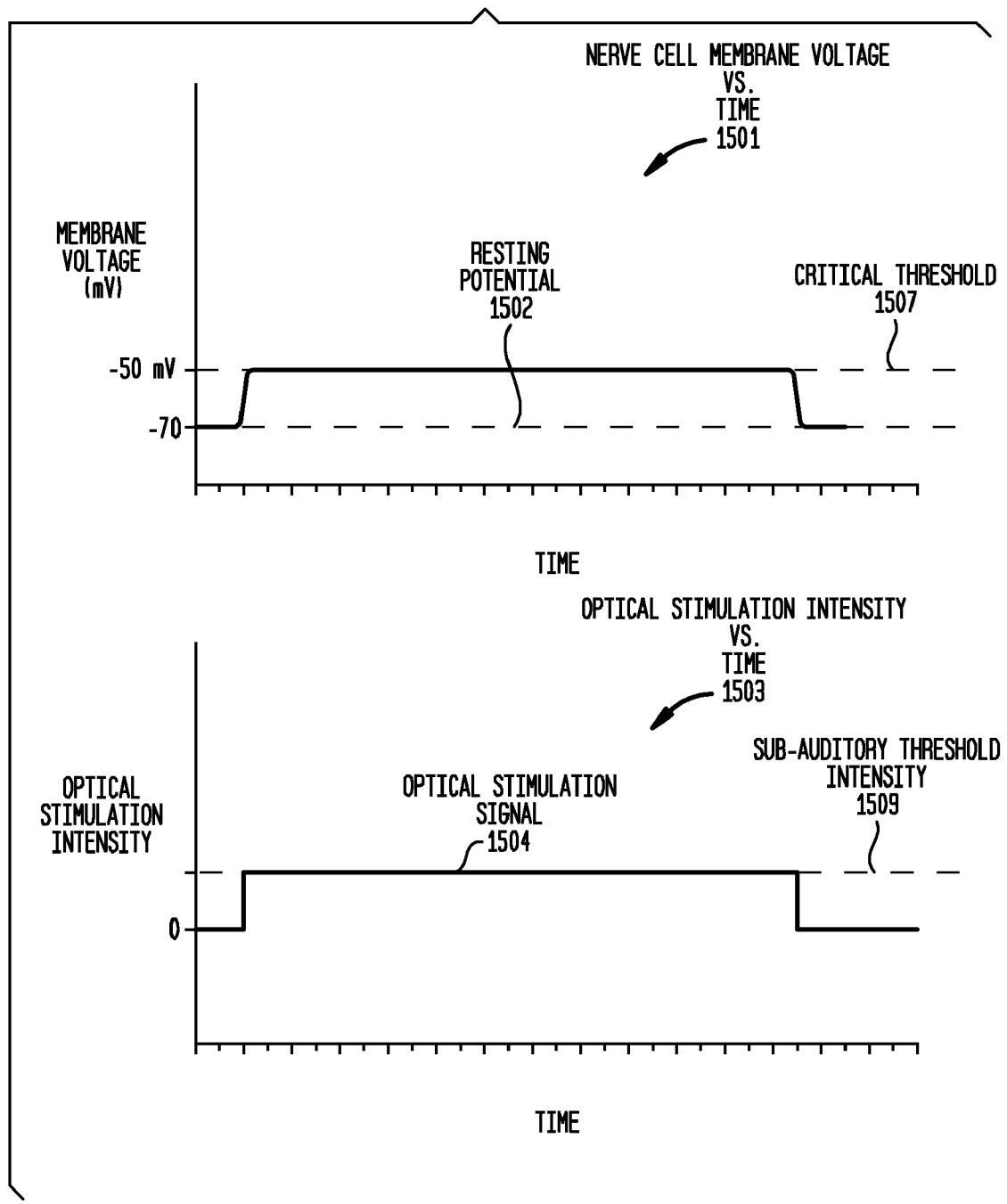
FIG. 15 is a diagram illustrating the membrane voltage versus time of a region of a recipient's nerve prior to and during the application of optical stimulation thereto, as well as an exemplary optical stimulation signal which may result in the illustrated membrane voltage, in accordance with embodiments of the present invention.

FIG. 15 is two graphs illustrating an optical stimulation signal 1504 delivered to a recipient's cochlea 140, and the resulting increase in membrane voltage. As shown, optical stimulation signal 1504 has an intensity 1509 which is below the recipient's auditory threshold level. This intensity is referred to as sub-auditory intensity 1509. As noted above, application of optical stimulation signal 1504 increase the membrane potential of the stimulated nerve cells to approximately the recipient's critical threshold 1507.

Figure 16:
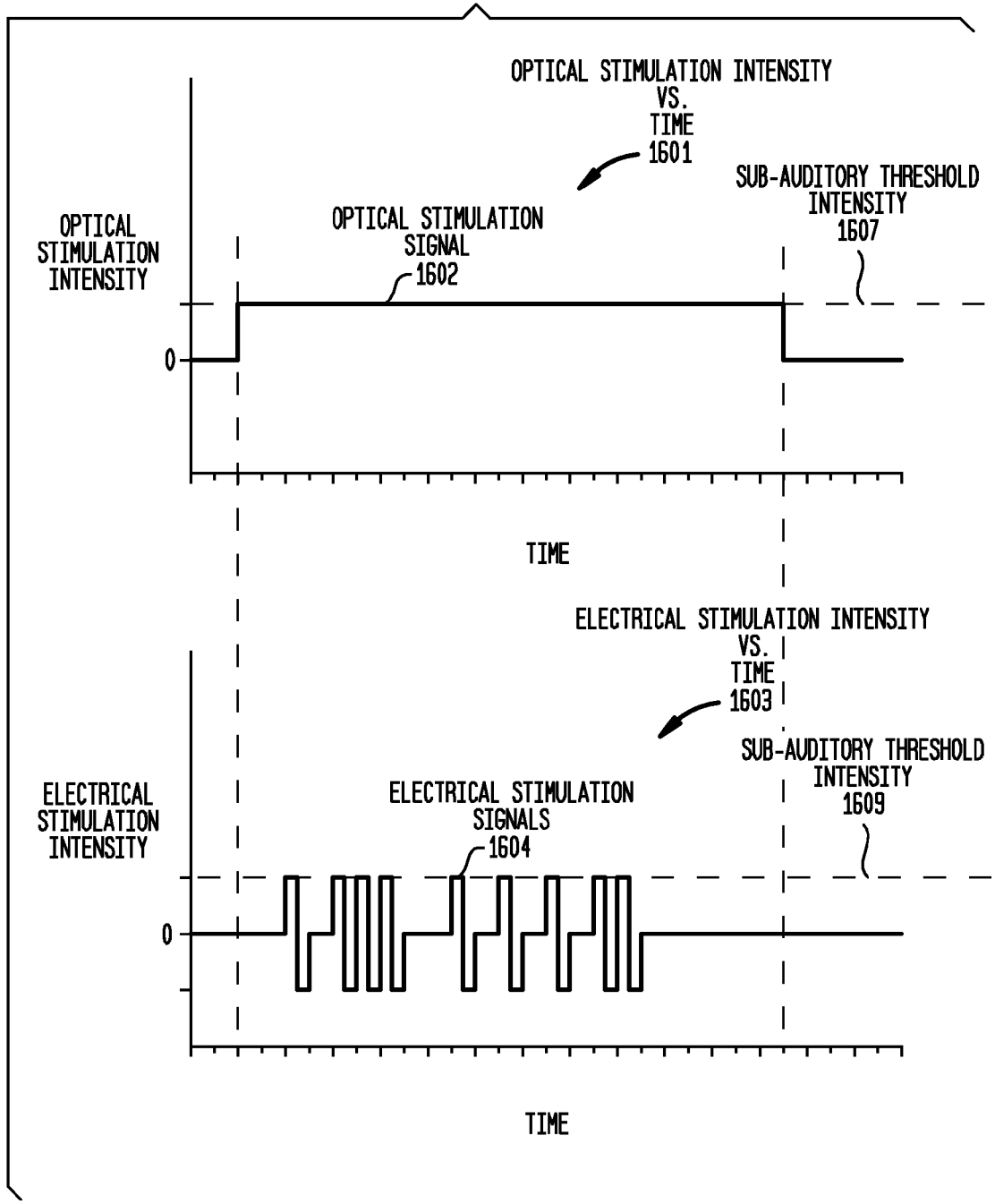
FIG. 16 is a diagram illustrating exemplary optical and electrical stimulation signals used to stimulate a recipient's nerve cells in accordance with embodiments of the present invention.

FIG. 16 is two graphs illustrating optical and electrical stimulation signals that may be generated and applied to a recipient's cochlea 140. Graph 1601 illustrates an optical stimulation 1602 which increases the membrane voltage of nerve cells of cochlea 140 to approximately less than or equal to the recipient's critical threshold. Graph 1603 illustrates electrical stimulation signals 1604 which, in combination with optical stimulation signal 1602, evoke a hearing response. As shown, both optical stimulation signal 1602 and electrical stimulation signals 1604 have sub-auditory threshold intensities 1607, 1609. In the embodiments of FIG. 16, electrical stimulation signals 1604 are generated and applied to the optically stimulated nerve cells after optical stimulation signal 1602 increases the membrane voltage of the nerve cells to the critical threshold.

Figure 17:
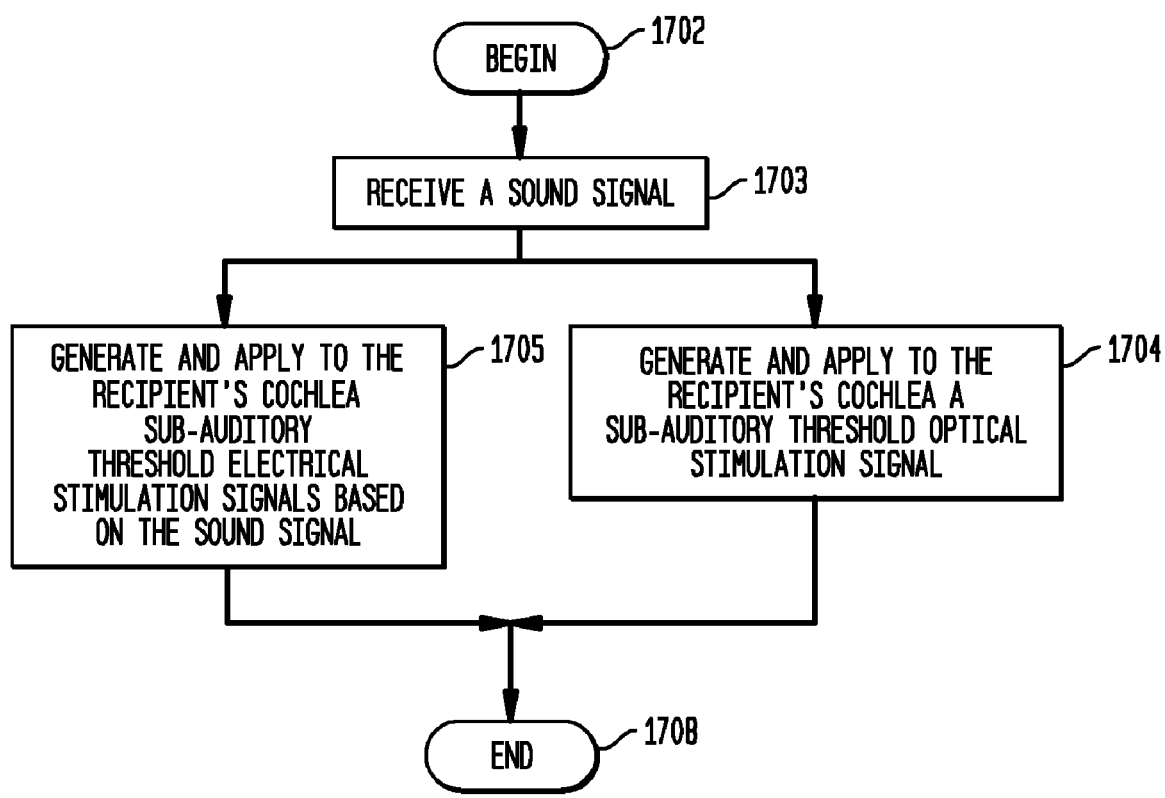
FIG. 17 is a flowchart illustrating the operations performed in a cochlear implant in accordance with embodiments of the present invention.

FIG. 17 is a flowchart illustrating a method performed during operation of cochlear implant 100 in accordance with embodiments of FIG. 16. The method begins at block 1702. At block 1703, a sound signal is received by the cochlear implant. At block 1704, a sub-auditory threshold optical stimulation signal is generated and applied to a recipient's cochlea 140 (FIG. 1). At block 1705, sub-auditory threshold electrical stimulation signals are generated based on the received sound signal, and are applied to cochlea 140. The method then ends at block 1708. As would be appreciated by one of ordinary skill in the art, the operations of blocks 1705 and 1704 occur concurrently, with appropriate delays for generation and/or application of electrical stimulation signals so that the membrane voltage of the nerve cells increases to the critical threshold.

The aspects of the present invention described above with reference to FIGS. 15-17 have been described with reference to delivery of an optical stimulation signal comprising a single pulse of electromagnetic (EM) radiation. It would be appreciated that in other embodiments multiple pulses of EM radiation may be used to increase the membrane voltage of nerve cells of cochlea 140. In these embodiments, optical stimulation signals would be generated and applied to cochlea 140 at a frequency which causes the membrane voltage to remain at or near or lower than the recipient's critical threshold.

Likewise, the embodiments of FIGS. 15-17 have been described with optical stimulation signals which increase the membrane voltage of the nerve cells of cochlea 140 to approximately the recipient's critical threshold. It would be appreciated that in other embodiments, the optical stimulation signals may have an intensity which increases the membrane voltage to levels other than at or close to the critical threshold.

Several aspects of the present invention have been described with reference to the cochlear implant illustrated in FIGS. 1, 3 and 4. In brief review, such a cochlear implant terminates in a stimulating assembly which comprises a longitudinally aligned and distally extending array of stimulating contacts disposed along a length thereof. In most applications of the present invention, the contact array comprises optical and electrical contacts via which stimulation signals are applied.

FIGS. 18A-18E illustrate embodiments of a stimulating assembly 1818 having different arrangements of optical contacts 1820 and electrical contacts 1830. For ease of illustration, electrical contacts 1830 are depicted as rectangles and optical contacts 1820 are depicted as ovals. These exemplary shapes are provided only to facilitate understanding of embodiments of the present invention and do not define or limit electrical contacts 1830 or optical contacts 1820 in any manner.

Figure 18A:
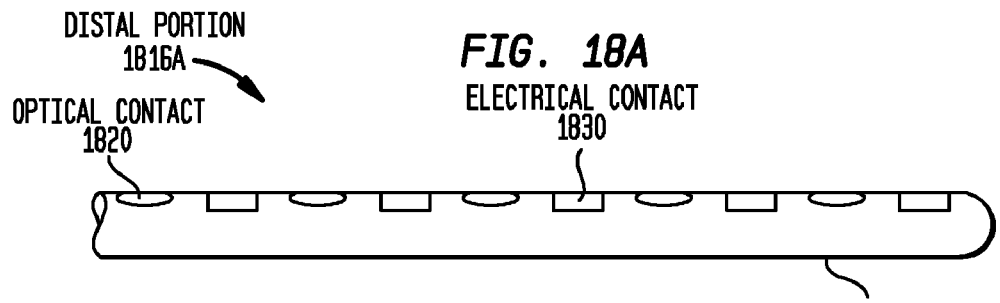
FIG. 18A is a side view of an implantable stimulating assembly in accordance with embodiments of the present invention.
Figure 18B:
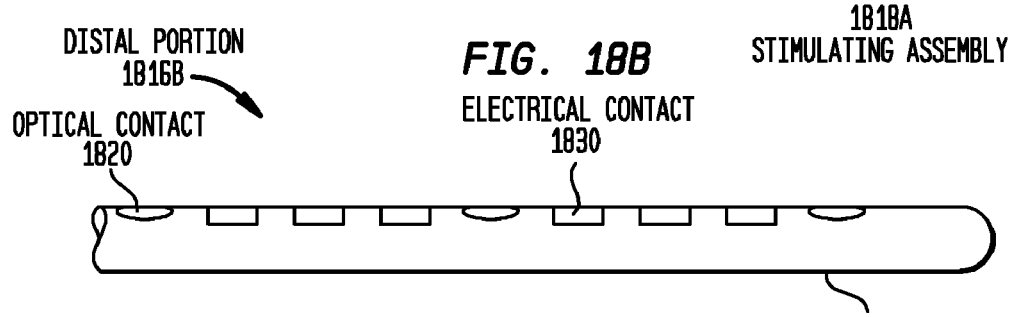
FIG. 18B is a side view of an implantable stimulating assembly in accordance with embodiments of the present invention.
Figure 18C:
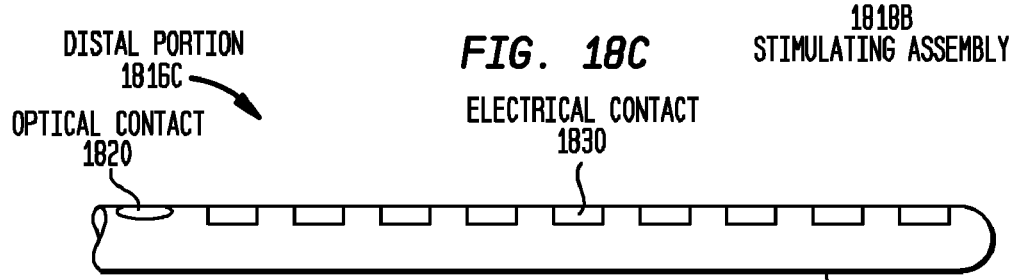
FIG. 18C is a side view of an implantable stimulating assembly in accordance with embodiments of the present invention.

In FIG. 18A, a distal portion 1816A of a stimulating assembly 1818A is illustrated. As shown, electrical contacts 1830 and optical contacts 1820 are arranged in an alternating fashion. In other words, in the illustrated arrangement of FIG. 18A, no optical contacts 1820 are adjacent other optical contacts. Similarly, no electrical contacts 1830 are adjacent other electrical contacts. In contrast, as shown in FIG. 18B, a smaller number of optical contacts 1820 are dispersed along distal portion 1816B within a contact array which is primarily comprised of electrical contacts 1830. In the embodiment illustrated in FIG. 18C, a single optical contact 1820 is shown. Optical contact 1820 is positioned at the proximal end of distal portion 1816C.

Figure 18D:
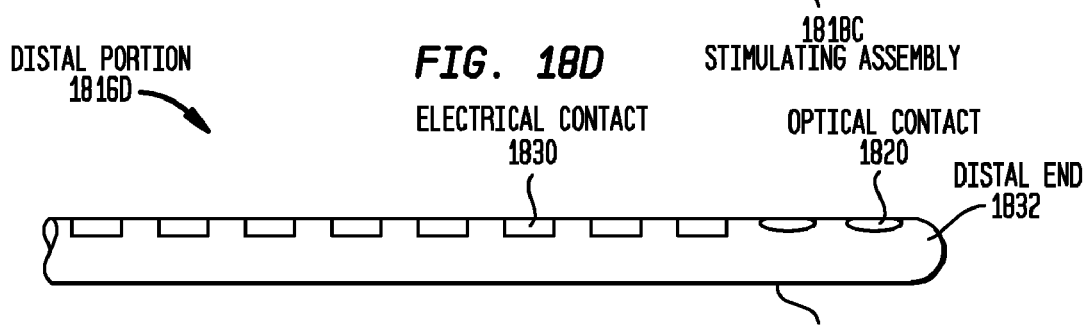
FIG. 18D is a side view of an implantable stimulating assembly in accordance with embodiments of the present invention.
Figure 18E:
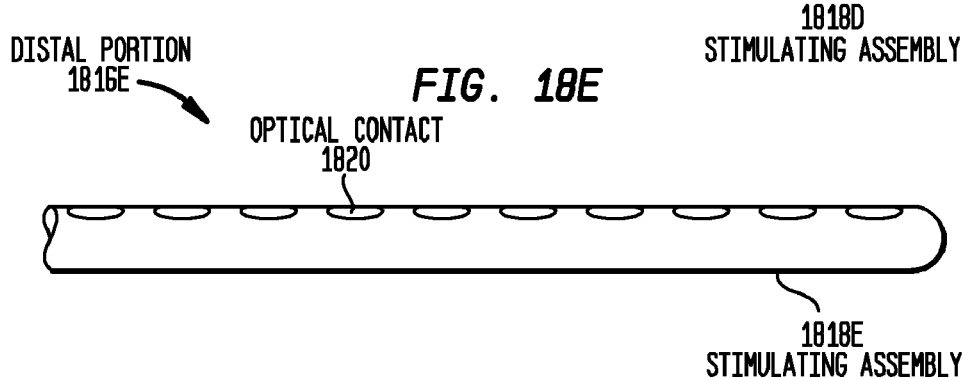
FIG. 18E is a side view of an implantable stimulating assembly in accordance with embodiments of the present invention.

In FIG. 18D, two optical contacts 1820 are shown. Optical contacts 1820 are positioned at the distal end 1832 of distal portion 1816D. This arrangement illustrated in FIG. 18D may be useful, for example, in the embodiments described in greater detail below with reference to FIGS. 19-21. In the embodiment illustrated in FIG. 18E, distal portion 1816E includes only optical contacts 1820. Stimulating assembly 1818E may be used in embodiments of the present invention in which electrical stimulation is unnecessary or undesired.

As would be appreciated, the embodiments of FIGS. 18A-18E are provided for illustrative purposes only, and any arrangement or combination of optical and/or electrical contacts 1820, 1830 may be used in the various aspects of the present invention. The number of contacts may depend on, for example, the desired application, the needs of the recipient, etc.

The above aspects of the present invention have been described herein without reference to the position of the stimulating assembly within a recipient's cochlea. However, because, as noted above with reference to FIGS. 2A and 2B, the cochlea is tonotopically organized, position and/or geometry of the stimulating assembly, or of particular contacts, may impact the recipient's response to stimulation signals. For example, in certain aspects of the present invention, a stimulating assembly may extend through the basal region of the recipient's cochlea towards the apical end of the cochlea. In these embodiments, the stimulating assembly is inserted at least to the first turn of the cochlea, and sometimes further. In alternative aspects of the present invention, a stimulating assembly, referred to as a short stimulating assembly, is implanted only in the basal region of the cochlea. Such alternative aspects of the present invention are described below with reference to FIGS. 19 and 20.

A short stimulating assembly is advantageously used to treat the portion of the hearing impaired population who suffer from sensorineual hearing loss only in the basal region of the cochlea. Due to the tonotopic organization of the cochlea, such individuals maintain the ability to perceive middle to lower frequency sounds naturally, but have limited or no ability to perceive high frequency sounds. For such individuals, cochlear implants which may be implanted without damage to the residual hearing of a recipient, but which are configured to stimulate regions of the cochlea which are sensitive to high frequencies are beneficial.

Figure 19:
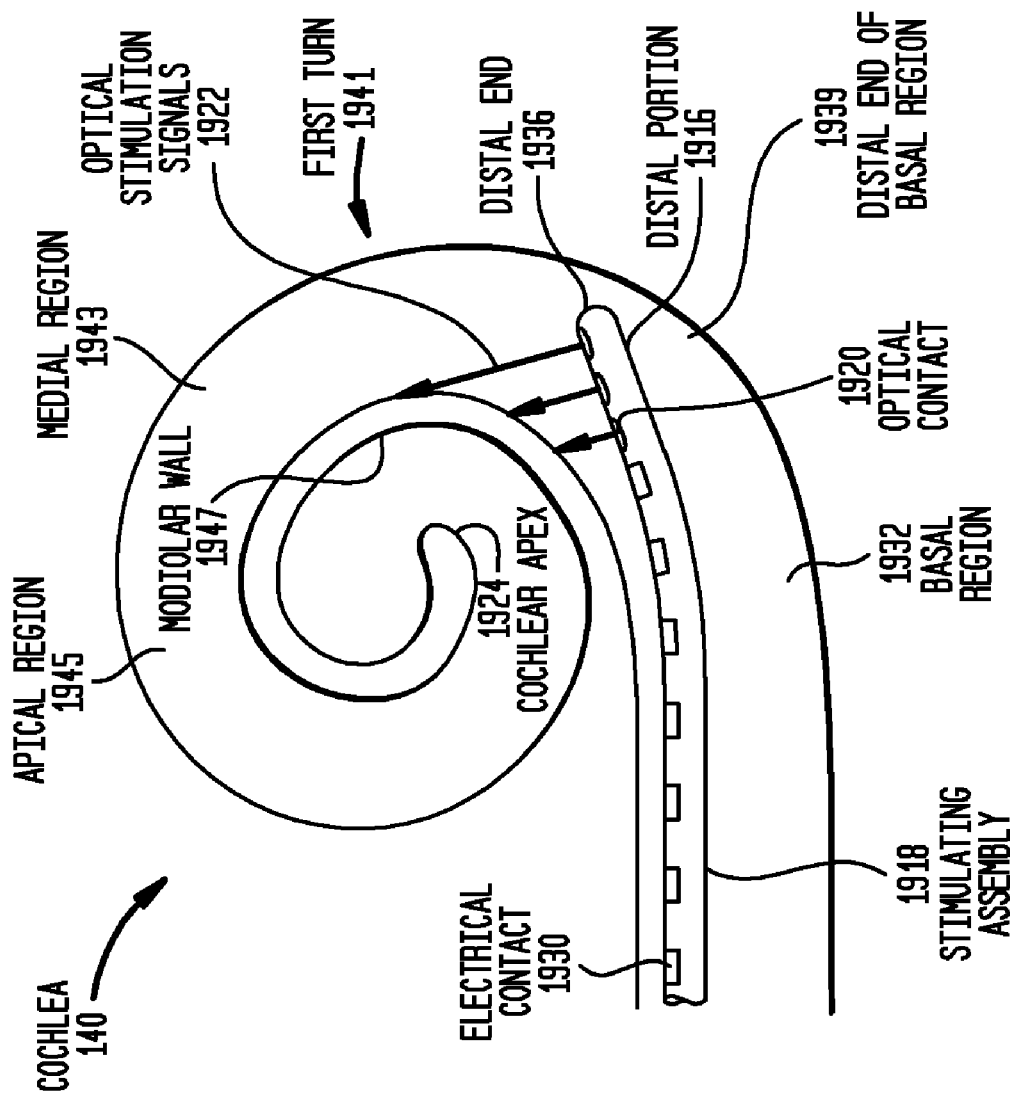
FIG. 19 is a simplified side view of cochlea having a short stimulating assembly in accordance with embodiments of the present invention implanted therein.

One such short stimulating assembly is shown in FIG. 19. Short stimulating assembly 1918 is configured to be fully implanted only in the basal region 1932 of a recipient's cochlea 140. For ease of illustration, a simplified view of cochlea 140 is shown. As such, the scala tympani and the scala vestibule have not been differentiated in FIG. 19. It would be appreciated that short stimulating assembly 1918 may be inserted into either the scala tympani or the scala vestibuli of cochlea 140.

When short stimulating assembly 1918 is fully implanted, distal end 1936 of the stimulating assembly is positioned at or near distal end 1939 of basal region 1932. Alternatively, when short stimulating assembly 1918 is fully implanted, distal end 1936 of the stimulating assembly is positioned within basal region 1932. As used herein, the basal region 1932 of cochlea 140 is the portions of the scala tympani and the scala vestibuli extending from the round window and oval window, respectively, to the first turn 1941 of cochlea 140. Therefore, when short stimulating assembly 1918 is fully implanted in only the basal region of cochlear 140, distal end 1936 of the short stimulating assembly is positioned at, in, or proximate to the region of cochlea 140 at which the first turn 1941 of cochlea 140 begins. As used herein, the positioning of distal end 1936 in this region of cochlea 140 includes positions of distal end 1936 in basal region 1932 or in first turn 1941.

Short stimulating assembly 1918 includes one or more optical contacts 1920 to apply optical stimulation signals 1922 to cochlea 140. In the embodiments of FIG. 19, short stimulating assembly 1918 has three optical contacts 1920 positioned at distal portion 1916. Distal portion 1916 is configured so that optical contacts 1920 are able to apply optical stimulation signals 1922 to the portions of the scala tympani and the scala vestibuli positioned proximate to cochlear apex 1924 (referred to as apical region 1945) and the portions of the scala tympani and the scala vestibuli positioned between basal region 1932 and apical region 1945 (referred to as medial region 1943).

Specifically, when short stimulating assembly 1918 is fully implanted, at least one optical contact 1920 is positioned opposite of modiolar wall 1947 of first turn 1941 such that there is a direct line of sight path between the optical contact 1920 and modiolar wall 1947. Due to the direct line of sight path, optical stimulation signals 1922 are delivered by the optical contact 1920 to modiolar wall 1947. In specific embodiments, the distal portion 1916 of short stimulating assembly 1918 is angled towards modiolar wall 1947 during or after insertion of the short stimulating assembly. The angling of distal portion 1916 improves the line of sight path between optical contacts 1920 and modiolar wall 1947.

As shown in FIG. 19, short stimulating assembly 1918 also includes a plurality of electrical contacts 1930. Electrical contacts 1930 are configured to apply electrical stimulation signals (not shown) to basal region 1932 of cochlea 140. It would be appreciated that the embodiments illustrated in FIG. 19 are merely illustrative and other arrangements of optical contacts 1920 and electrical contacts 1930 may be used. For example, in alternative embodiments, one or more optical contacts 1920 may be disposed along short stimulating assembly 1918 in basal region 1932. In other embodiments, short stimulating assembly 1918 may comprise a single optical contact 1920 positioned at distal end 1936. In still other embodiments, short stimulating assembly 1918 may include no electrical contacts.

In the exemplary embodiment of FIG. 19, electrical stimulation signals are applied to basal region 1932 to evoke a hearing percept of high frequency components of a sound signal. Similarly, optical stimulation signals 1922 are delivered to medial region 1943 of cochlea 140 to evoke perception of middle to low frequency components of a sound signal. These illustrative embodiments may be particularly beneficial for patients with progressing hearing loss. As noted above, a short stimulating assembly having only electrical contacts thereon (generally referred to as an electrode assembly) is generally implanted in a recipient who suffers only high frequency hearing loss. A short electrode assembly is used over a longer electrode assembly so that the medial and apical regions of the cochlea that naturally perceive middle and low frequency sounds remain intact. However, over time certain individuals lose the ability to naturally perceive middle and low frequency sounds. In such individuals who previously received a short electrode assembly, the electrode assembly must be removed from the cochlea and replaced with a longer electrode assembly that can electrically stimulate the middle or low frequency regions of the cochlea. Short stimulating assembly 1918 may reduce the need for such future surgery. Specifically, short stimulating assembly 1918 may be implanted in basal region 1932 in a minimally invasive manner without damaging the medial 1943 and apical 1945 regions of cochlea 140. Stimulating assembly 1918 would be configured to stimulate (optically and/or electrically) high frequency responsive basal region 1932. If at a later time the recipient losses the ability to perceive middle and/or low frequencies, optical contacts 1920 may be used to optically stimulate medial 1943 and/or apical 1945 regions of cochlea 140. Providing such optical stimulation to medial 1943 and/or apical 1945 regions of cochlea 140 does not require an additional surgical procedure, but rather requires a reprogramming of the cochlear implant.

It should be appreciated that in certain embodiments of the present invention, it is not necessary to obtain a direct line of sight path between optical contacts 1920 and medial 1943 and/or apical 1945 regions of cochlea 140 in order to evoke perception of middle or low frequencies. As would be appreciated, nerves corresponding to the low and middle frequencies pass behind modiolar wall 1947 of basal turn 1941. As such, in embodiments of the present invention, the spatially selectivity provided by optical stimulation signals may be used to stimulate the middle and/or low frequency nerves passing behind modiolar wall 1947.

As described above, aspects of the present invention generate and apply optical and/or electrical stimulation signals to cochlea 140 to provide a variety of therapeutic benefits. For example, optical stimulation signals may be applied to generate pseudospontneous nerve activity, to evoke a hearing percept, to maintain neural survival, etc. Electrical stimulation signals may be applied to evoke a hearing percept, maintain neural survival, etc. Furthermore, combinations of optical and electrical stimulation signals may be applied to collectively evoke a hearing percept. It should be appreciated that short stimulating assembly 1918 may be used in any of the above or other aspects of the present invention.

Figure 20:
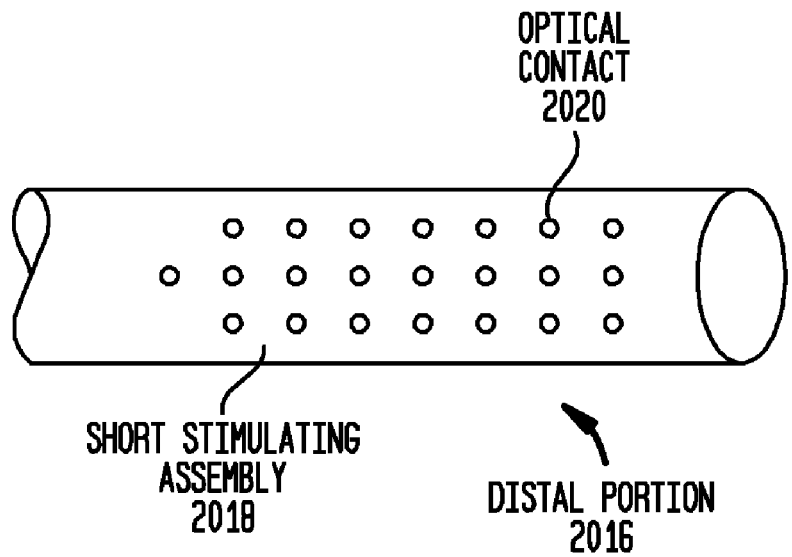
FIG. 20 is a top-view of a distal region of a short stimulating assembly in accordance with embodiments of the present invention.

FIG. 20 is a top-view of a distal region 2016 of a short stimulating assembly 2018 in accordance with embodiments of the present invention. In the illustrated embodiment, distal region 2016 comprises multiple optical contacts 2020, however in other embodiments a single contact may be utilized. Each contact 2020 is configured to direct optical stimulation signals to medial and or apical regions of cochlea 140 (FIG. 1). As would be appreciated, the arrangement of optical contacts 2020 shown in FIG. 20 is merely illustrative.

Aspects of the present invention have described herein with reference to the cochlear implant illustrated in FIGS. 1, 3 and 4. Specifically, in review, a cochlear implant 400 shown in FIG. 4 includes an electromagnetic radiation (EMR) generator 462 which generates optical stimulation signals 463. The optical stimulation signals 463 comprise electromagnetic energy which is generated and delivered to cochlea 140. As noted above, the electromagnetic energy may have any wavelength, and is not limited to electromagnetic energy within the optical spectrum. For example, in specific embodiments of the present invention, EMR generator 463 is a light source. The wavelength of the light used in these embodiments is not necessarily limited to the visible range of approximately 350 to 750 nanometers (nm), but rather may include ultraviolet, visible, infrared, far infrared or deep infrared light. For example, in certain embodiments, infrared light having wavelengths between about 750 nm and 1500 nm may used. In other embodiments, light having longer or shorter wavelengths may also be used.

Figure 21:
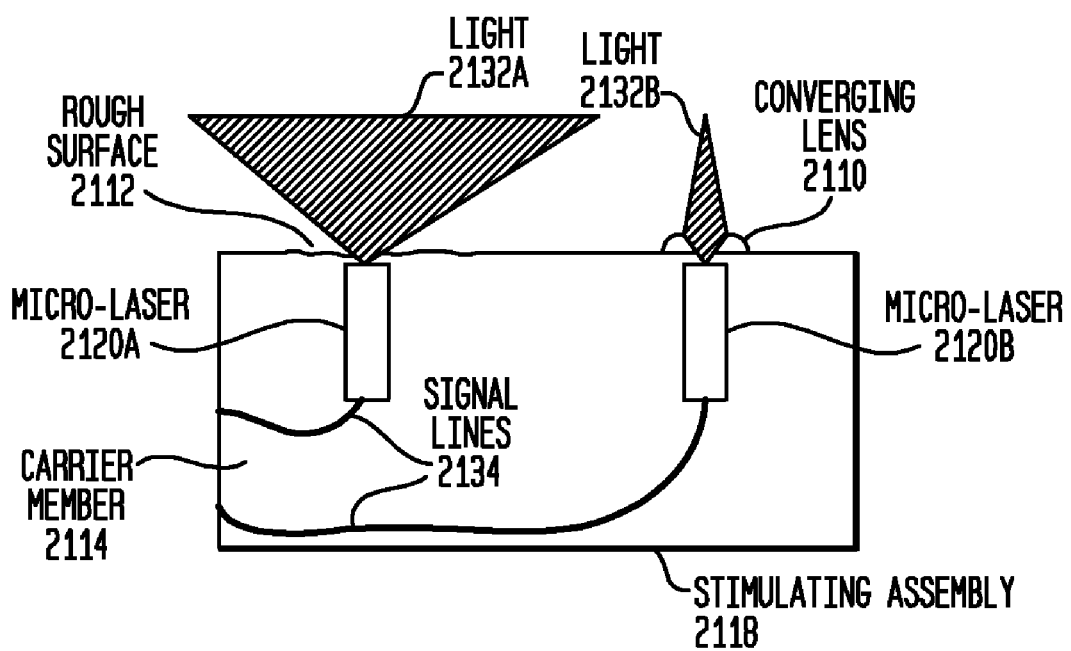
FIG. 21 is a schematic diagram illustrating a region of a stimulating assembly in accordance with embodiments of the present invention.

In the embodiments described above with reference to FIG. 4, the light source would comprise part of a stimulator unit 402 that also includes an electrical stimulation signal generator 460. However, as noted above, other arrangements may be implemented in embodiments of the present invention. FIG. 21 illustrates such an alternative arrangement of a portion of a stimulating assembly 2118.

In the embodiments of FIG. 21, two light sources, shown as micro-lasers 2120 are integrated into carrier member 2114 of stimulating assembly 2118. Micro-lasers 2120 generate optical stimulation signals in the form of light 2132 which may be delivered to a cochlea (not shown). Micro-lasers 2120 may controlled by control signals received via signal lines 2134.

As shown in FIG. 21, the light emitting portion of micro-laser 2620A is positioned adjacent a rough surface 2112 of stimulating assembly 2118. Rough surface 2118 functions as an optical contact which disperses light 2132A. In contrast, the light emitting portion of micro-laser 2120B is positioned adjacent a converging lens 2110 integrated in, or disposed on the surface of carrier member 2114. Converging lens 2610 functions as an optical contact which substantially focuses light 2132B.

Although FIG. 21 is illustrated with reference to micro-lasers 2620 embedded in carrier member 2114, it should be appreciated that other light generating or emitting sources, such as Light Emitting Diodes (LEDs) may also be embedded in the carrier member in place of the micro-lasers.

Figure 22:
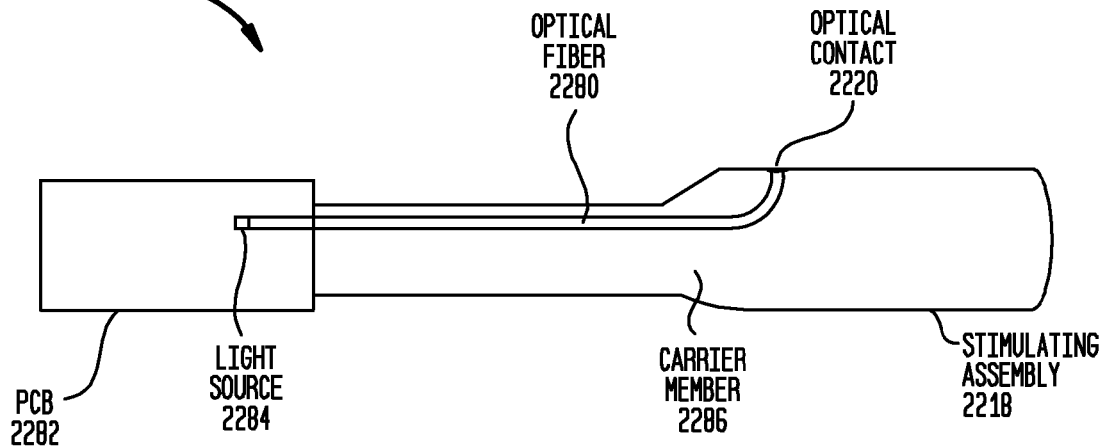
FIG. 22 is a simplified schematic diagram illustrating an implantable component of a cochlea implant in accordance with embodiments of the present invention.
Figure 23:
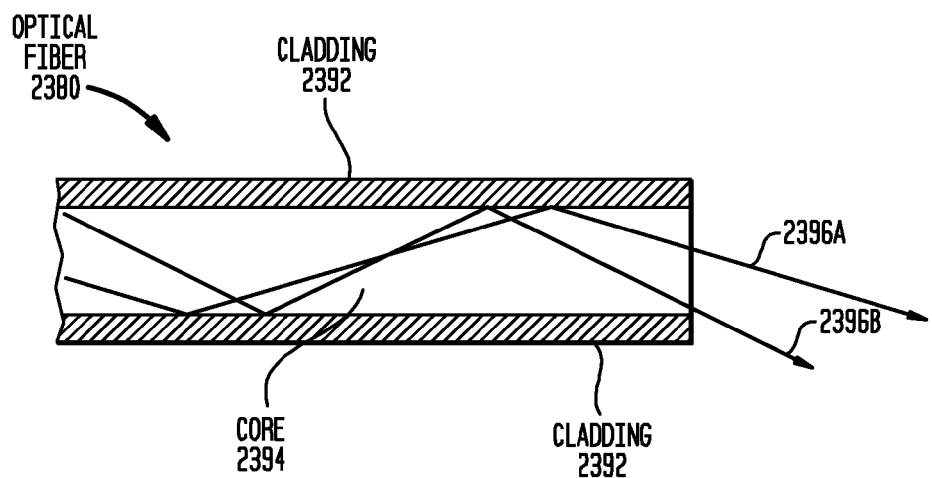
FIG. 23 is cross-sectional view of an optical fiber which may be advantageously used in embodiments of the present invention.

FIG. 22 illustrates elements of an internal component 2200 of a cochlea implant in accordance with embodiments of the present invention. As shown, similar to the above embodiments, the EM generator 2284, shown as light source 2284, is not integrated or embedded in carrier member 2286 of stimulating assembly 2218. Rather, light source 2282 comprises part of a stimulator unit, illustrated as printed circuit board (PCB) 2282. Embedded in carrier member 2286 is an optical fiber 2280 which couples light source 2284 to an optical contact 2220 of stimulating assembly 2218. In the embodiments of FIG. 22, light source 2284 generates optical stimulation signals which are directed to optical contact 2220 by optical fiber 2280. FIG. 23 illustrates an exemplary optical fiber which may be used in embodiments of the present invention.

For ease of illustration, internal component 2200 is shown in FIG. 22 as comprising one light source 2284, one optical fiber 2280, and one optical contact 2220. As described above, a stimulating assembly in accordance with embodiments of the present invention may comprise a plurality of optical contacts 2220. As such, in embodiments of the present invention, carrier member 2286 may have a plurality of optical fibers 2280 embedded therein to couple the optical contacts to light source 2284. Furthermore, in some such embodiments in internal component 2200 may further include multiple light sources 2284 and multiple optical fibers 2280.

As is well known in the art, an optical fiber is a type of waveguide. Waveguides include low bending loss fibers, photonic crystal fibers, telecom fibers, metal coated silica core fibers, etc. It should be appreciated that although FIG. 22 illustrates the use of one type of optical fiber 2280 to direct light to optical contact 2220, any other type of waveguide could also be used in alternative embodiments.

In certain embodiments of the present invention, silicone carrier member 2286 of stimulating assembly 2218 is used to guide optical stimulation signals from an optical light source to the nerve cells of a recipient. In such an embodiment, the silicone acts as a mechanism to spread the optical stimulation signals. In further embodiments, the carrier member surface, or portions thereof, could be lined with a reflecting layer to minimize the loss or spread of light.

As noted above, FIG. 23 illustrates an exemplary optical fiber 2380 used in embodiments of the present invention. FIG. 23 provides a cross-sectional view of a portion of optical fiber 2380. As is known in the art, optical fiber 2380 carries light along its length. Optical fibers may be made from glass (silica) or polymers such as polymers having high refractive indices, such as Polyethersulfone (PES) and Polyphenylsulfone (PPS). As would be appreciated, any known waveguide or optical-fiber structure may be used. As used herein, an optical-fiber structure is an inclusive term that includes a single optical fiber as well as a bundle of individual optical fibers, a fused bundle of optical fibers, star couplers, and includes ferrules, lenses, and the like used to couple light into and out of the optical fiber structure.

As shown, optical fiber 2380 comprises a core 2394 through which light 2396 travels. Light 2396 is retained in core 2394 by total internal reflection caused by cladding 2392. In operation, light 2396 exits core 2394 at one or more optical contacts (not shown). Exemplary optical contacts are described below with reference to FIGS. 27A and 27B.

In some embodiments, optical fiber 2380 is hermetically sealed. Materials which may be used to hermetically seal optical fiber 2380 include, for example, parylene, diamond-like carbon, and platinum.

In certain embodiments, optical fiber 2380 may support many propagation paths or transverse modes. Such fibers are referred to as multimode fibers (MMF). In contrast, fibers which support only a single mode are called single mode fibers (SMF). Embodiments of the present invention may use either a SMF or an MMF.

As is well known, light can be lost through the cladding of an optical fiber at bends in the optical fiber. As such, the thickness of cladding 2392 may vary depending on the light, application, acceptable losses, etc. Similarly, cladding 2392 may be doped to create an index of refraction which is useful in the desired application. In embodiments of the present invention, the optical fiber, or portions thereof, may comprise a low bending loss fiber to prevent the loss of light. These low loss bending fibers may comprise, for example, photonic specialty fibers. In still other embodiments of the present invention, the cladding of the optical fiber 2380 may be replaced with a reflective coating to reduce the size of the optical fiber. Such a coating could optionally function not only as a reflector for light, but also as a conductor for electrical stimulation signals.

In further embodiments of the present invention, the stimulating assembly may comprise diffractive or refractive optics to steer light to specific locations.

Figure 24A:
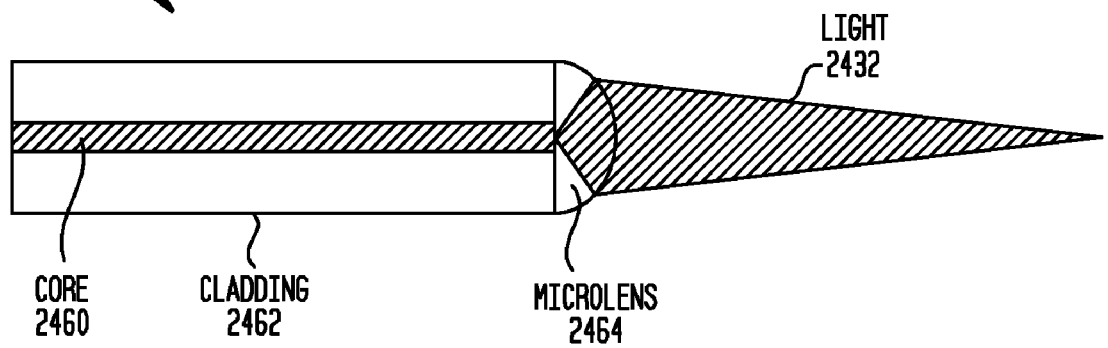
FIG. 24A is a schematic view of a distal region of an optical fiber which may be advantageously used in embodiments of the present invention.
Figure 24B:
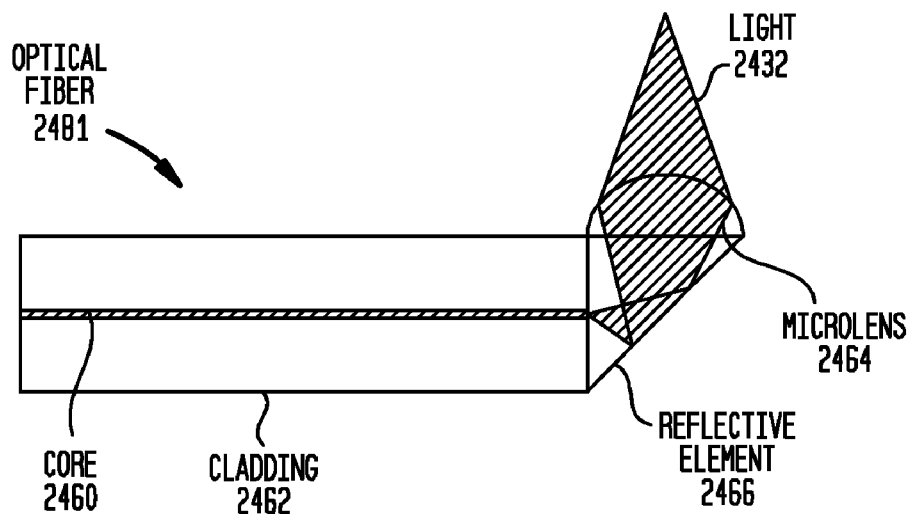
FIG. 24B is a schematic view of a distal region of an optical fiber which may be advantageously used in embodiments of the present invention.

FIGS. 24A and 24B illustrate distal regions of two optical fibers 2480, 2481 in accordance with embodiments of the present invention. Optical fiber 2480 is shown in FIG. 24A. As shown, light 2432 is transmitted through core 2460 and retained therein core by total internal reflection caused by cladding 2462. As shown, optical fiber 2480A comprises a standard telecom fiber in combination with a micro-lens 2464 which acts as an optical contact which focuses light 2432.

Optical fiber 2481 is illustrated in FIG. 24B. Optical fiber 2481 is substantially similar to optical fiber 2480 expect that optical fiber 2481 includes a reflective element 2466. In this embodiment, as light 2432 is transmitted through core 2460, the light impinges upon reflective element 2466 to reflect the light an angle of 90°. Reflective element 2466 directs light to micro-lens 2464 which acts as an optical contact to focus light 2432. Reflective element 2466 may comprise a mirror, a glass/polymer to air interface, or a reflective coating deposited on an interior surface of optical fiber 2481.

As discussed above, at least two approaches may be taken to optically stimulate a recipient's nerve cells. In one embodiment explained above with reference to FIG. 21, a light source may be embedded in a carrier member adjacent an optical contact. In other embodiments described above with reference to FIGS. 22-24B, the light source may be located at a distance from an optical contact with a waveguide delivering the light from the source to the optical contact. In either of these embodiments, various different types of light sources may be used. Specifically, any light source that meets the shape, size, wavelength and/or intensity demands of the specific embodiment may be used. Exemplary lights sources include, but are not limited to, light emitting diodes (LEDs), laser diodes and lasers or microlasers (collectively lasers herein) such as Vertical Cavity Surface Emitting Lasers (VCSELs), free electron lasers (FELs), etc.

Figure 25:
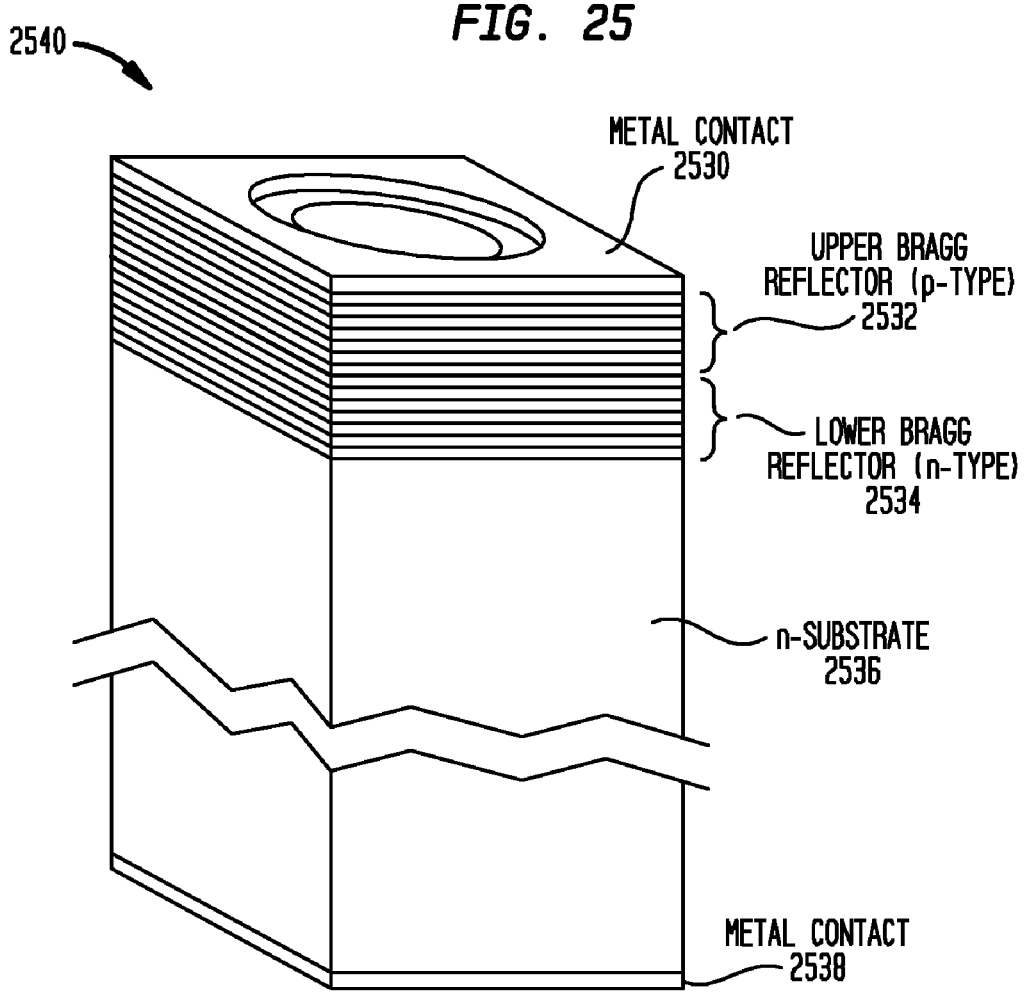
FIG. 25 is a cross-sectional view of a micro-laser that may be used in embodiments of the present invention.

FIG. 25 illustrates the structure of an exemplary VCSEL 2540 which may be used in accordance with embodiments of the present invention. VCSEL 2540 is a type of semiconductor laser diode having laser beam emission perpendicular from a top surface of metal contact 2530. This is contrary to conventional edge-emitting semiconductor lasers which emit lights from surfaces formed by cleaving the individual chip out of a wafer. As shown, VCSEL 2540 consists of two distributed Bragg reflector (DBR) mirrors 2532, 2534 positioned parallel to a wafer surface or substrate 2536. As shown, the upper and lower mirrors 2532 and 2534 are doped as p-type and n-type materials, respectively, forming a diode junction.

Figure 26:
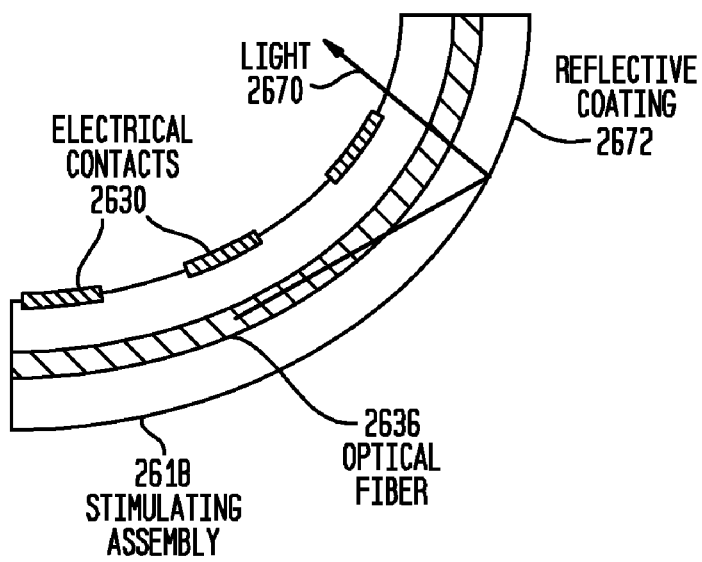
FIG. 26 is a cross-sectional view of a region of a stimulating assembly illustrating the direction of travel of light in accordance with certain embodiments of the present invention.

As noted above, several different waveguides may be used to guide light to an optical contact. As is well known in the art, waveguides are sensitive to bending losses. In other words, when a waveguide is bent, light will pass through the cladding. FIG. 26 illustrates an embodiment of the present invention may be configured to take advantage of such bending losses. Specifically, in the embodiment of FIG. 26, a portion of the light, shown by arrow 2670, passes through the cladding (not shown) of optical fiber 2636 and impinges onto a surface of stimulating assembly 2618. In this embodiment, the interior or outer surface of stimulating assembly 2618 has a reflective coating 2672. When the portion of light 2670 impinges on this reflective surface, the light is reflected back through the optical fiber towards electrical contacts 2630 and impinges upon nerve cells of the recipient.

Figure 27A:
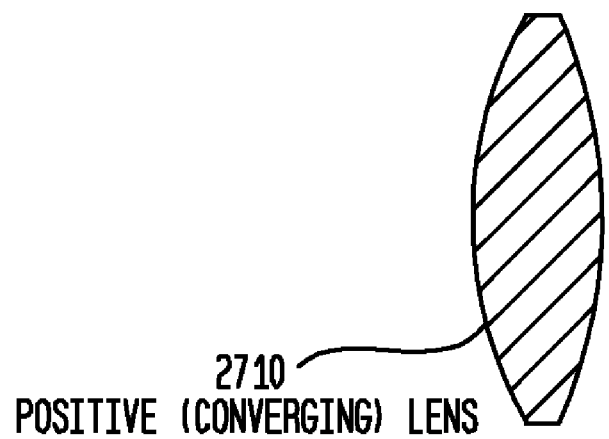
FIG. 27A is an enlarged cross-sectional view of a converging lens that may be used in an optical contact in accordance with embodiments of the present invention.
Figure 27B:
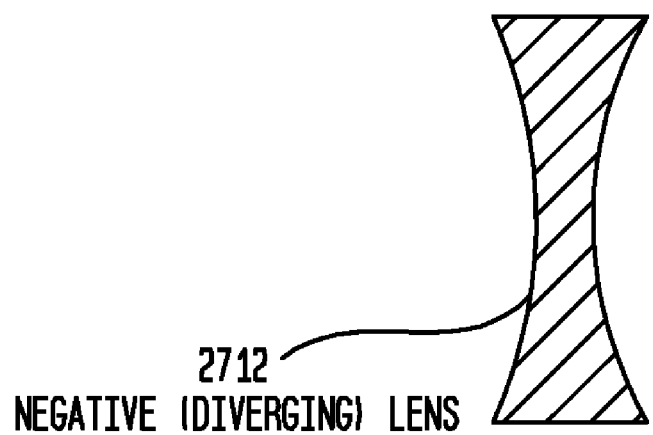
FIG. 27B is an enlarged cross-sectional view of a diverging lens that may be used in an optical contact in accordance with embodiments of the present invention.

FIGS. 27A and 27B illustrate exemplary lenses which may be used as optical contacts in accordance with embodiments of the present invention. Specifically, FIG. 27A is an enlarged view of a converging lens 2710 that may be used in an optical contact in accordance with embodiments of the present invention. Similarly, FIG. 27B is an enlarged view of a diverging lens 2712 that may be used in an optical contact in accordance with embodiments of the present invention.

As would be appreciated, it may be possible to omit lens from the stimulating assembly by polishing the end of the waveguide appropriately. However, the use of a lens provides more design options and may provide an enhanced ability to direct optical stimulation signals. The lens may be manufactured by molding the lens from silicone. The shape of a lens may be determined by considering the physical property of the material used, and the interface property of the material to the perilymph (lens profile, change in refractive index at the interface, surface roughness). In embodiments of the present invention, a spherical lens or aspeherical lens may be used.

In further embodiments of the present invention, the optical contacts may be movable, slidable, re-shapeable, or otherwise adjustable to allow for adjustment of the direction of the optical stimulation signals after implantation.

As would be appreciated, optical contacts may be negatively impacted by the build up of fibrous tissue thereto. As such, in certain embodiments of the present invention, the optical contacts are treated with anti-fibrotic treatments to protect the contacts from being impacted by fibrous tissue. These treatments could be delivered via surface geometry or via drugs.

As discussed above, conventional electrically stimulating devices require initial and/or periodic fitting or programming procedures to determine the current required to evoke a hearing percept. This generally requires determination of one or both of a recipient's threshold (T) level, and comfort (C). The fitting procedure may use either subjective or objective feedback (neural response telemetry (NRT) measurements) to obtain the T and C levels.

As with electrical stimulation, the T and C levels may also need to be established for optically stimulating channels of a cochlear implant. A fitting procedure using subjective and/or objective feedback (NRT measurements) would be used to obtain the T and C levels.

In certain embodiments of the present invention, the time required for such a fitting procedure may be reduced by using several advantages provided by NRT. Specifically, in certain embodiments, the recipient's cochlea is stimulated via an electrical contact, and the response of the nerve cells is measured at recording contact. Following this, optical stimulation would be provided via an optical contact and the resulting response would also be measured. The ratio of both T and C's for the electrical contact and the optical contact could then be correlated. This information would be used to assist in finding the T and C values for other optical and electrical contacts.

As noted above, a neural-stimulating device in accordance with embodiments of the present invention delivers optical and/or electrical stimulation signals to nerve cells of a recipient. In accordance with embodiments of the present invention, the stimulated nerve may be cells of any nerve, such as motor or sensory nerves in the peripheral nervous system, nerve tissue of the central nervous system (nerves within the brain and spinal cord), the cranial nerves (e.g., the optic nerve, the olfactory nerve, the auditory nerve, and the like), the autonomic nervous system, as well as brain tissue and/or any other neural tissue. Thus, the tissue to which optical and/or electrical stimulation signals are applied need not itself be a "nerve" as conventionally defined, but could include brain tissue that when stimulated by light or current initiates a response similar to that carried by a nerve, e.g., an action potential that includes electrical and/or chemical components, and which is propagated to a location some distance from the point that was optically stimulated.

Further features and advantages of the present invention may be found in commonly owned and co-pending U.S. patent Application entitled "A NEURAL-STIMULATING DEVICE FOR GENERATING PSEUDOSPONTANEOUS NEURAL ACTIVITY," and commonly owned and co-pending U.S. patent Application entitled "COMBINED OPTICAL AND ELECTRICAL NEURAL STIMULATION," both filed concurrently herewith. Both of these applications are hereby incorporated by reference herein in their entirety.

All documents, patents, journal articles and other materials cited in the present application are hereby incorporated by reference.

Embodiments of the present invention have been described with reference to several aspects of the present invention. It would be appreciated that embodiments described in the context of one aspect may be used in other aspects without departing from the scope of the present invention.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart there from.

What is claimed is:

1. A cochlear implant, comprising:
    a stimulator unit configured to generate electrical stimulation signals based on sound processor-encoded signals, and to generate one or more optical stimulation signals; and
    an implantable stimulating assembly configured to be implanted into a basal region of a recipient's cochlea such that when said stimulating assembly is fully implanted a distal end of said assembly extends to the first turn of the cochlea, said stimulating assembly comprising:
        an optical contact positioned on said stimulating assembly configured to deliver said one or more optical stimulation signals to the cochlea, and
        an electrical contact positioned on said stimulating assembly configured to deliver said electric stimulation signals to a basal region of the cochlea so as to cause perception by the recipient of one or more frequency components of an acoustic sound signal on which said sound processor-encoded signals are based.

2. The implant of claim 1, wherein said stimulator unit comprises:
    an electrical stimulation generator configured to generate said electrical stimulation signals; and
    an electromagnetic radiation source configured to generate said one or more optical stimulation signals.

3. The implant of claim 2, wherein said electromagnetic radiation source is a light source and said one or more optical stimulation signals generated by said light source are in the optical spectrum.

4. The implant of claim 1, further comprising:
    at least one microphone configured to receive the acoustic sound signal;
    a sound processor configured to generate said set of sound-processor encoded signals, wherein said encoded signals are based on said acoustic sound signal.

5. The implant of claim 4, wherein said stimulating assembly has a longitudinal axis extending there though, and further wherein said optical contact is configured to direct at least a portion of each of said one or more optical stimulation signals substantially away from said basal region of the cochlea substantially parallel with said longitudinal axis of said assembly.

6. The implant of claim 5, wherein said optical contact is configured to direct a majority of each of said optical stimulation signals substantially away from said basal portion of the cochlea substantially parallel with said longitudinal axis.

7. The implant of claim 1, wherein when said implantable stimulating assembly is implanted in the cochlea, said optical contact is configured to deliver said one or more optical stimulation signals to the basal region of the cochlea.

8. The implant of claim 7, wherein when said implantable stimulating assembly is implanted in the cochlea, said electrical contact and said optical contact are each configured to deliver said electrical stimulation signals and said one or more optical stimulation signals to the same basal region of the cochlea.

9. The implant of claim 1, wherein when said implantable stimulating assembly is implanted in the cochlea, said optical contact is configured to deliver said one or more optical stimulation signals to an apical region of the cochlea.

10. The implant of claim 9, wherein one or more of said optical contact is positioned at a distal end of said stimulating assembly.

11. The implant of claim 10, wherein said at least one optical contact is selectively adjustable so as to focus said one or more optical stimulation signals at a desired area of said apical region.

12. The implant of claim 1, further comprising:
    a waveguide coupling said optical contact to said stimulator unit configured to direct said one or more optical stimulation signals to said optical contact.

13. The implant of claim 12, wherein said waveguide comprises an optical fiber.

14. The implant of claim 1, further comprising:
    a plurality of optical contacts disposed on said stimulating assembly.

15. The implant of claim 14, wherein said one or more optical stimulation signals comprise a plurality of optical stimulation signals, and wherein one of said plurality of optical contacts is configured to deliver said plurality of optical stimulation signals to auditory nerve cells of the cochlea.

16. The implant of claim 14, wherein said one or more optical stimulation signals comprise a plurality of optical stimulation signals, and wherein each of said plurality of optical contacts are configured to deliver one of said plurality of optical stimulation signals to auditory nerve cells of the cochlea.

17. The implant of claim 14, wherein said one or more optical stimulation signals comprise a plurality of sets of optical stimulation signals, and wherein each of said plurality of optical contacts are configured to deliver one of said sets of optical stimulation signals to auditory nerve cells of the cochlea.

18. The implant of claim 14, further comprising:
    a waveguide coupling said stimulator unit to each of said plurality of contacts.

19. The implant of claim 14, further comprising:
    optical fibers separately coupling each of said plurality of contacts to said stimulator unit.

20. The implant of claim 1, wherein said optical contact is configured to substantially focus said one or more optical stimulation signals.

21. The implant of claim 1, wherein said optical contact is configured to disperse said one or more optical stimulation signals.

22. The implant of claim 1, wherein said one or more optical stimulation signals cause sub-threshold stimulation of the cochlea.

23. The implant of claim 22, wherein said one or more optical stimulation signals that cause said sub-threshold stimulation are delivered at an intensity to attain substantial neural survival in the stimulated region of the cochlea.

24. The implant of claim 1, wherein said one or more optical stimulation signals generated by said stimulator unit comprise a set of optical stimulation signals.

25. The implant of claim 1, wherein said stimulator unit is configured to concurrently generate said one or more optical stimulation signals and said one or more electrical stimulation signals.

26. The implant of claim 1, wherein said stimulator unit is configured to generate said one or more optical stimulation signals based on said set of sound processor-encoded signals, and wherein delivery of said one or more optical stimulation to the cochlea causes perception by the recipient of one or more frequency components of said acoustic sound signal.

27. A method for stimulating a recipient's cochlea using a cochlear implant having a stimulating assembly configured such that when said assembly is fully implanted a distal end of said assembly extends to the first turn of the cochlea, the method comprising:
  generating electrical stimulation signals based on a set of encoded signals;
  delivering said electric stimulation signals to a basal region of the cochlea so as to cause perception by the recipient of one or more frequency components of an acoustic sound signal on which said sound encoded signals are based;
  generating one or more optical stimulation signals; and
  delivering said one or more optical stimulation signals to the cochlea.

28. The method of claim 27, wherein said delivering said one or more optical stimulation signals to the cochlea comprises:
  delivering said one or more optical stimulation signals to a basal region of the cochlea.

29. The method of claim 28, further comprising:
  delivering said electrical stimulation signals and said optical stimulation signals to the same basal region of the cochlea.

30. The method of claim 27, wherein said delivering said one or more optical stimulation signals to the cochlea comprises:
  delivering said one or more optical stimulation signals to an apical region of the cochlea.

31. The method of claim 30, wherein said stimulating assembly has a longitudinal axis extending there though, said method further comprising:
  directing at least a portion of each of said one or more optical stimulation signals substantially away from said basal portion of the cochlea substantially parallel with said longitudinal axis of said assembly.

32. The method of claim 31, wherein said method further comprises:
  directing a majority of each of said optical stimulation signals substantially away from said basal portion of the cochlea substantially parallel with said longitudinal axis.

33. The method of claim 27, further comprising:
  receiving said acoustic sound signal;
  generating said set of encoded signals based on said acoustic sound signal.

34. The method of claim 27, wherein said delivering said one or more optical stimulation signals comprises:
  delivering said one or more optical stimulation signals at an intensity configured to cause sub-threshold stimulation of the auditory nerves of the cochlea.

35. The method of claim 34, wherein said method further comprises:
  delivering said one or more optical stimulation signals an intensity to attain substantial neural survival in the auditory nerves of the cochlea.

36. The method of claim 27, wherein said delivering said one or more optical stimulation signals to the cochlea comprises:
  delivering said one or more optical stimulation signals via an optical contact configured to cause dispersed optical stimulation.

37. The method of claim 27, wherein delivering said one or more optical stimulation signals to the cochlea comprises:
  delivering said one or more optical stimulation signals via an optical contact configured to cause substantially focused optical stimulation.

38. The method of claim 37, further comprising:
  focusing said optical stimulation signals at a first apical region of the cochlea; and
  focusing said optical stimulation signals at a second apical region of the cochlea.

39. The method of claim 27, further comprising:
  concurrently delivering said electrical stimulation signals and said one or more optical stimulation signals to the cochlea.

40. The method of claim 27, further comprising:
  generating said one or more optical signals based on said set of sound processor-encoded signals, and wherein delivery of said one or more optical stimulation signals to the cochlea causes perception by the recipient of one or more frequency components of said acoustic sound signal.

41. A cochlear implant having a stimulating assembly configured such that when said assembly is fully implanted a distal end of said assembly extends to the first turn of the cochlea, the implant comprising:
  means for generating electrical stimulation signals based on a set of encoded signals;
  means for delivering said electric stimulation signals to a basal region of the cochlea so as to cause perception by the recipient of one or more frequency components of an acoustic sound signal on which said sound processor-encoded signals are based;
  means for generating one or more optical stimulation signals; and
  means for delivering said one or more optical stimulation signals to the cochlea.

42. The implant of claim 41, wherein said means for delivering said one or more optical stimulation signals to the cochlea comprises:
  means for delivering said one or more optical stimulation signals to a basal region of the cochlea.

43. The implant of claim 41, further comprising:
  means for delivering said electrical stimulation signals and said optical stimulation signals to the same basal region of the cochlea.

44. The implant of claim 41, wherein said means for delivering said one or more optical stimulation signals to the cochlea comprises:

means for delivering said one or more optical stimulation signals to an apical region of the cochlea.

45. The implant of claim 41, further comprising:
means for receiving the acoustic sound signal;
means for generating said set of encoded signals based on said acoustic sound signal.

46. The implant of claim 41, wherein said means for delivering said one or more optical stimulation signals comprises:
means for delivering said one or more optical stimulation signals at an intensity configured to cause sub-threshold stimulation of the auditory nerves of the cochlea.

47. The implant of claim 41, further comprising:
means for generating said one or more optical signals based on said set of sound processor-encoded signals, and wherein delivery of said one or more optical stimulation signals to the cochlea causes perception by the recipient of one or more frequency components of said acoustic sound signal.

* * * * *